United States Patent
Vannuffelen et al.

(10) Patent No.: US 7,609,380 B2
(45) Date of Patent: Oct. 27, 2009

(54) REAL-TIME CALIBRATION FOR DOWNHOLE SPECTROMETER

(75) Inventors: Stephane Vannuffelen, Tokyo (JP); Takeaki Nakayama, Machida (JP); Tsutomu Yamate, Yokohama (JP); Toru Terabayashi, Sagamihara (JP); Akira Otsuka, Machida (JP); Kentaro Indo, Machida (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 409 days.

(21) Appl. No.: 11/273,893

(22) Filed: Nov. 14, 2005

(65) Prior Publication Data

US 2007/0109537 A1   May 17, 2007

(51) Int. Cl.
 *G01J 3/28*   (2006.01)
(52) U.S. Cl. .................................. 356/326; 250/269.1
(58) Field of Classification Search .............. 356/326; 250/269.1
See application file for complete search history.

(56) References Cited

U.S. PATENT DOCUMENTS

| | | | |
|---|---|---|---|
| 3,780,575 A | 12/1973 | Urbanosky | |
| 3,859,851 A | 1/1975 | Urbanosky | |
| 3,932,754 A | 1/1976 | Riedl et al. | |
| 4,008,394 A | 2/1977 | Risgin et al. | |
| 4,101,221 A | 7/1978 | Schunck et al. | |
| 4,241,997 A | 12/1980 | Chraplyvy | |
| 4,860,581 A | 8/1989 | Zimmerman et al. | |
| 4,994,671 A | 2/1991 | Safinya et al. | |
| 5,167,149 A | 12/1992 | Mullins et al. | |
| 5,185,645 A | 2/1993 | Sartorius et al. | |
| 5,201,220 A | 4/1993 | Mullins et al. | |
| 5,331,156 A | 7/1994 | Hines et al. | |
| 5,859,430 A * | 1/1999 | Mullins et al. ............... 250/255 |
| 6,031,609 A * | 2/2000 | Funk et al. ................... 356/310 |
| 6,437,326 B1* | 8/2002 | Yamate et al. ........... 250/269.1 |
| 6,476,384 B1 | 11/2002 | Mullins et al. | |
| 2004/0061858 A1* | 4/2004 | Pope et al. ................... 356/435 |
| 2005/0088660 A1* | 4/2005 | Ronnekleiv ................. 356/478 |
| 2005/0242807 A1* | 11/2005 | Freedman .................... 324/303 |

FOREIGN PATENT DOCUMENTS

| | | |
|---|---|---|
| EP | 1211502 A2 | 6/2002 |
| JP | 56-150332 A | 11/1981 |

* cited by examiner

*Primary Examiner*—Kara E Geisel
(74) *Attorney, Agent, or Firm*—Matthias Abrell; Jaime Castano; Dale Gaudier

(57) ABSTRACT

An apparatus for performing real-time analysis of a subterranean formation fluid includes a light source configured to transmit at least a sample signal through a sample of the subterranean formation fluid and a reference signal, at least one photodetector configured to continuously detect the sample and reference signals, and an electronics assembly configured to compensate for drift in the detected sample signal in real-time based on the value of the detected reference signal.

27 Claims, 17 Drawing Sheets

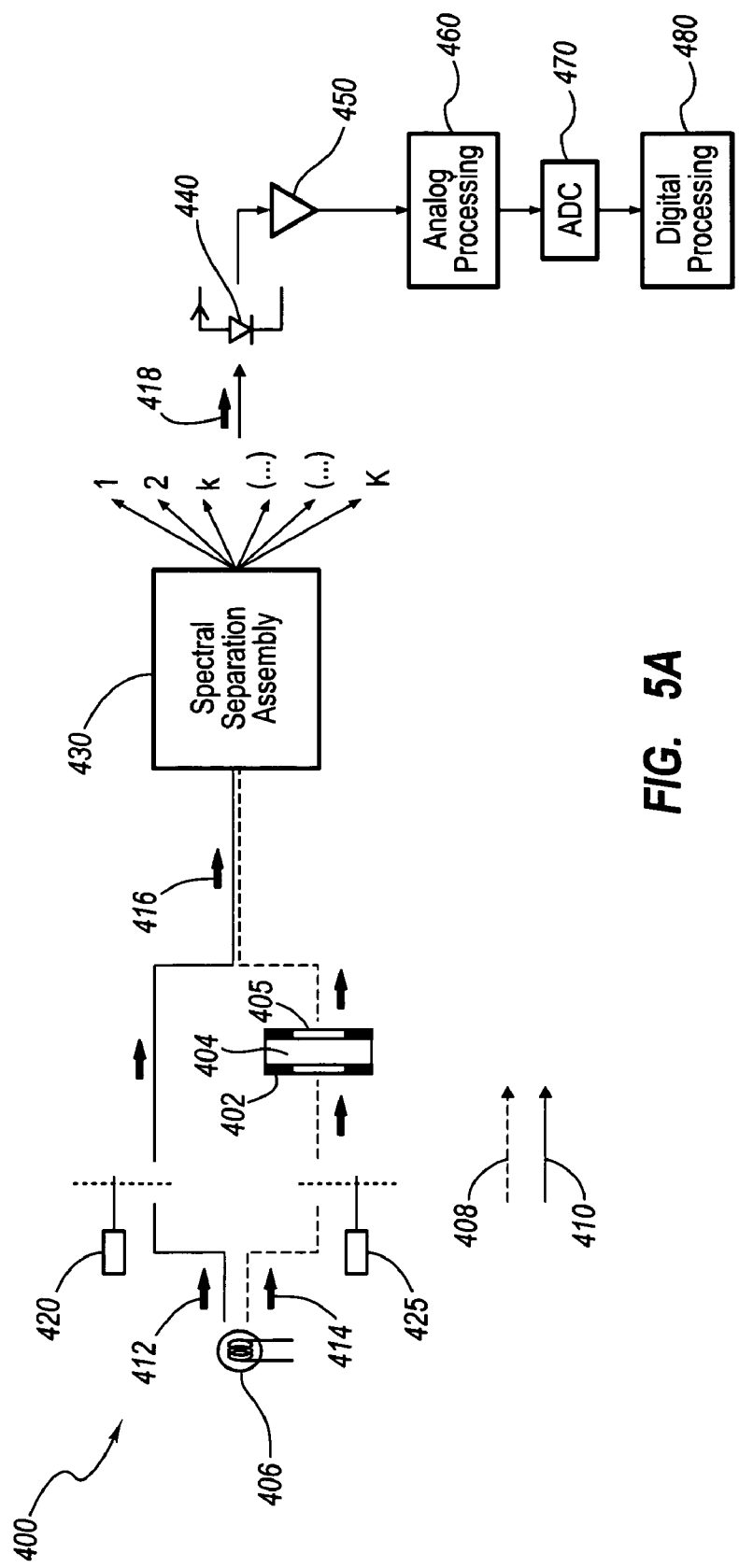
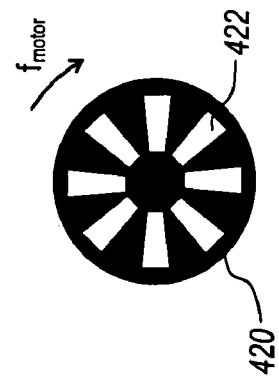
FIG. 5A
FIG. 5B

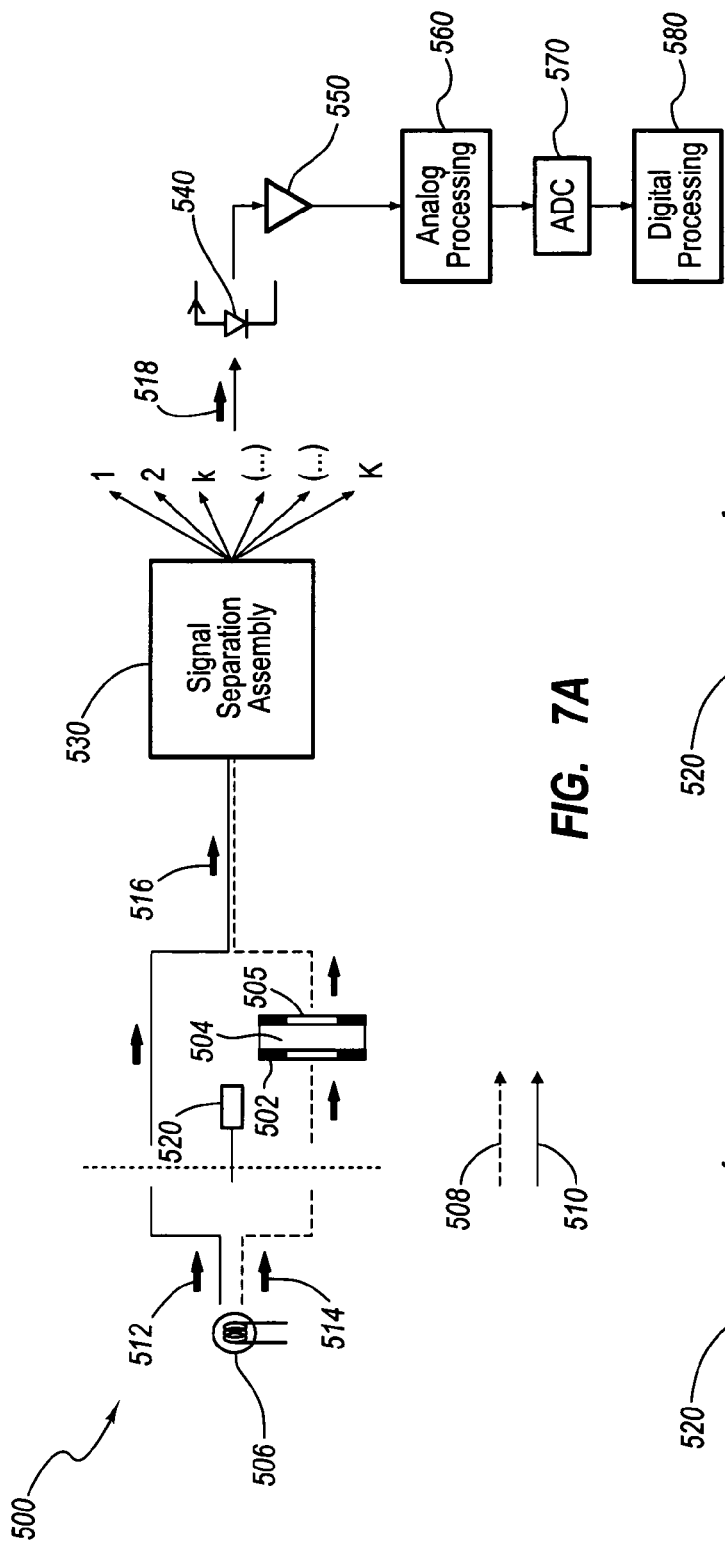
FIG. 7A
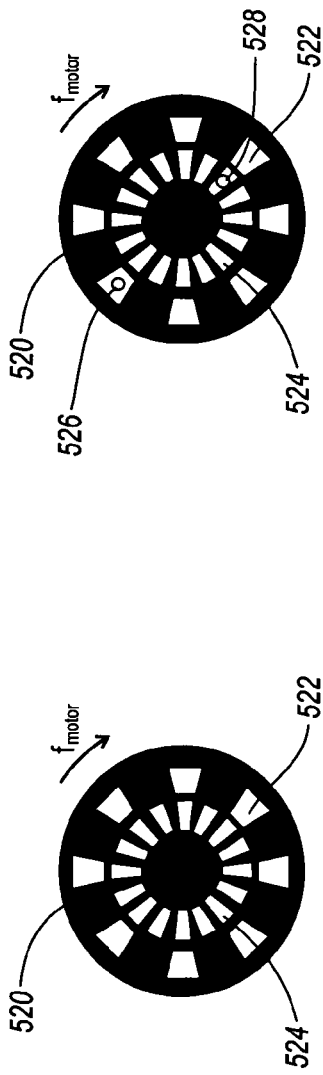
FIG. 7B
FIG. 7C

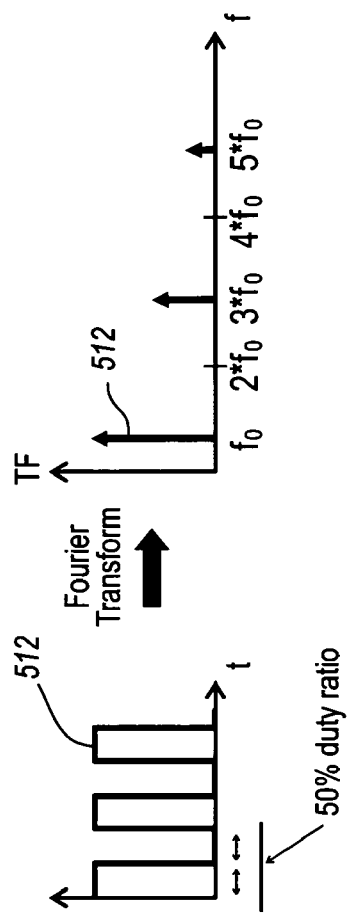
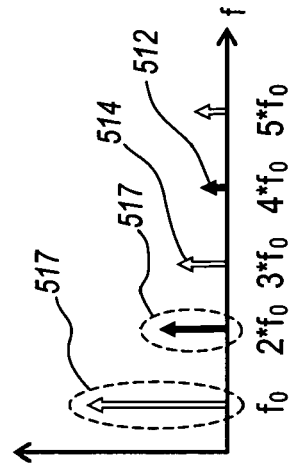
FIG. 8B
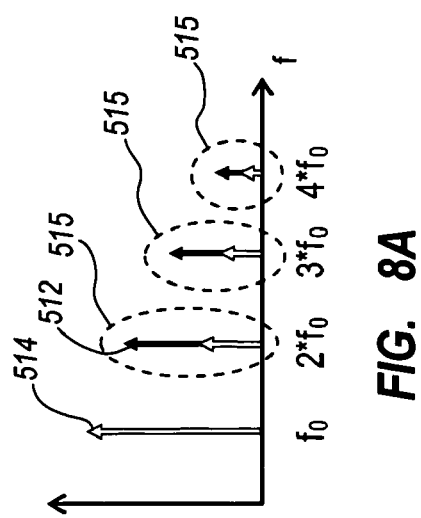
FIG. 8C
FIG. 8A

SIGNAL ACQUISITION AND PROCESSING DURING ONE STEP. SAME METHODS AS THE ONE DESCRIBED FOR STATIC CASE MAY APPLY.

REAL-TIME CALIBRATION FOR DOWNHOLE SPECTROMETER

FIELD OF THE INVENTION

The present invention relates generally to subterranean formation evaluation and testing in the exploration and development of hydrocarbon-producing wells, such as oil or gas wells. More particularly, the invention relates to methods and apparatuses for compensating for temperature drift in the various devices used to analyze fluids produced in such wells.

BACKGROUND OF THE INVENTION

In order to evaluate the nature of underground formations surrounding a borehole, it is often desirable to obtain and analyze samples of formation fluids from various specific locations in the borehole. Over the years, various tools and procedures have been developed to facilitate this formation fluid evaluation process. Examples of such tools can be found in U.S. Pat. No. 6,476,384 ("the '384 patent"), the entirety of which is hereby incorporated by reference.

As described in the '384 patent, Schlumberger's repeat formation tester (RFT) and modular formation dynamics tester (MDT) tools are specific examples of sampling tools. In particular, the MDT tool includes a fluid analysis module for analyzing fluids sampled by the tool. FIG. 16 illustrates a schematic diagram of such a downhole tool 10 for testing earth formations and analyzing the composition of fluids from the formation. Downhole tool 10 is suspended in a borehole 12 from a logging cable 15 that is connected in a conventional fashion to a surface system 18. Surface system 18 incorporates appropriate electronics and processing systems for control of downhole tool 10 and analysis of signals received from downhole tool 10.

Downhole tool 10 includes an elongated body 19, which encloses a downhole portion of a tool control system 16. Elongated body 19 also carries a selectively-extendible fluid admitting/withdrawal assembly 20 (shown and described, for example, in U.S. Pat. Nos. 3,780,575, 3,859,851, and 4,860,581, each of which is incorporated herein by reference) and a selectively-extendible anchoring member 21. Fluid admitting/withdrawal assembly 20 and anchoring member 21 are respectively arranged on opposite sides of elongated body 19. Fluid admitting/withdrawal assembly 20 is equipped for selectively sealing off or isolating portions of the wall of borehole 12, such that pressure or fluid communication with the adjacent earth formation is established. A fluid analysis module 25 is also included within elongated body 19, through which the obtained fluid flows. The obtained fluid may then be expelled through a port (not shown) back into borehole 12, or sent to one or more sample chambers 22, 23 for recovery at the surface. Control of fluid admitting/withdrawal assembly 20, fluid analysis module 25, and the flow path to sample chambers 22, 23 is maintained by electrical control systems 16, 18.

Over the years, various fluid analysis modules have been developed for use in connection with sampling tools, such as the MDT tool, in order to identify and characterize the samples of formation fluids drawn by the sampling tool. For example, U.S. Pat. No. 4,994,671 (incorporated herein by reference) describes an exemplary fluid analysis module that includes a testing chamber, a light source, a spectral detector, a database, and a processor. Fluids drawn from the formation into the testing chamber by a fluid admitting assembly are analyzed by directing light at the fluids, detecting the spectrum of the transmitted and/or backscattered light, and processing the information (based on information in the database relating to different spectra) in order to characterize the formation fluids. U.S. Pat. Nos. 5,167,149 and 5,201,220 (both of which are incorporated by reference herein) also describe reflecting light from a window/fluid flow interface at certain specific angles to determine the presence of gas in the fluid flow. In addition, as described in U.S. Pat. No. 5,331,156, by taking optical density (OD) measurements of the fluid stream at certain predetermined energies, oil and water fractions of a two-phase fluid stream may be quantified. As the techniques for measuring and characterizing formation fluids have become more advanced, the demand for more precise formation fluid analysis tools has increased.

As known in the art, the light sources, photodetectors and processing electronics employed in conventional fluid analysis modules are typically adversely affected by the extreme temperatures experienced in downhole environments. For example, the optical power of light sources (such as broad-spectrum incandescent light sources) tends to diminish or drift when operated at elevated temperatures. Similarly, the optical gains of photodetectors, such as Indium Gallium Arsenide (InGaAs) photodiodes, may drift by as much as a few nanometers per Kelvin when subjected to high operating temperatures. Processing electronics, and in particular analog processing electronics, are also known to be susceptible to DC offset drift when operated at extreme temperatures. Because an accurate estimation of the optical density of a formation fluid requires extremely precise measurements, such drifts in the light source, photodetector and/or processing electronics may result in errors in the estimation of the optical density of a formation fluid.

Although various calibration techniques for compensating for these temperature-dependent drifts and shifts are known in the art, these conventional calibration techniques are typically only performed prior to sampling and analyzing the formation fluid. However, because the temperature of the borehole or the sampling tool frequently changes after the calibration operation has been performed, the optical density estimations calculated after such temperature changes may be erroneous. For example, heat from the formation fluid itself, or heat generated by one or more of the components in the sampling tool during its operation, may cause the temperature of the fluid analysis module or sampling tool to change. In addition, because the temperature of the sampling tool itself slowly adjusts to its surrounding temperature due to its relatively large thermal mass, the temperature of the sampling tool and the fluid analysis module housed therein may continue to change even after a calibration operation has been performed. Any such temperature change will likely lead to the aforementioned drifts in optical power, optical gain and DC offset voltage.

Accordingly, there exists a need for an apparatus and method for compensating for temperature drift in the various devices and components used to analyze a downhole formation fluid. More particularly, there exists a need for an apparatus and method capable of continuous calibration.

SUMMARY OF THE INVENTION

The present invention provides a number of embodiments directed towards improving, or at least reducing, the effects of one or more of the above-identified problems. According to at least one embodiment, an apparatus for performing real-time analysis of a subterranean formation fluid comprises a light source configured to transmit at least a sample signal through a sample of the subterranean formation fluid and a reference signal, at least one photodetector configured to continuously detect the sample and reference signals, and an electronics assembly configured to compensate for drift in the detected sample signal in real-time based on the value of the detected reference signal. The light source may be a wavelength tunable light source or a broad-spectrum light source, for example, an incandescent lamp, a light-emitting diode (LED), a monochromator, or a tunable laser diode. The modulator may also comprise a digital modulator.

The apparatus may further comprise a modulator for modulating the sample and reference signals and a signal separation assembly for separating the modulated sample signal from the modulated reference signal. In certain embodiments, the signal separation assembly comprises a spectrometer, for example, a fixed wavelength spectrometer and/or a tunable spectrometer. In certain embodiments, the modulator modulates the sample signal and the reference signal at different frequencies. The modulator may also generate a phase shift between the sample signal and the reference signal. In some embodiments, the modulator comprises a first optical chopper configured to modulate the sample signal at a first frequency, and a second optical chopper configured to modulate the reference signal at a second frequency differing from the first frequency. In alternative embodiments, the modulator comprises a single optical chopper comprising a first circular row of apertures configured to modulate the sample signal and a second circular row of apertures configured to modulate the reference signal, wherein the number of apertures in the first circular row differs from the number of apertures in the second circular row.

In at least one embodiment, the modulator comprises a single optical chopper, wherein the sample signal is positioned to contact the single optical chopper at a first position, the reference signal is positioned to contact the single optical chopper at a second position, and the second position is separated from the first position by a desired phase shift angle. This single optical chopper may also comprise a single aperture for modulating the sample and reference signals. According to certain embodiments, the apparatus further comprises a sample photodetector positioned to detect the phase of the sample signal and a reference photodetector positioned to detect the phase of the reference signal. According to certain embodiments, the electronics assembly is configured to compensate for drift in the detected sample signal based on the value of the detected reference signal and an offset voltage generated by the electronics assembly.

In certain embodiments, a method for analyzing a subterranean formation fluid comprises transmitting a sample signal through a sample of the subterranean formation fluid, continuously transmitting a reference signal, continuously detecting the sample and reference signals using at least one photodetector, and correcting drift in the detected sample signal in real-time based on the value of the detected reference signal. This method may also comprise inserting a downhole sampling tool into a borehole, and drawing down the sample of the subterranean formation fluid.

According to some embodiments, the. method further comprises modulating the sample and reference signals. This method may also further comprise separating the modulated sample signal from the modulated reference signal using a signal separation assembly. In addition, modulating the sample and reference signals may comprise modulating the sample signal and the reference signal at different frequencies. Modulating the sample and reference signals may also comprise generating a phase shift between the sample signal and the reference signal. In at least one embodiment, modulating the sample and reference signals comprises modulating the sample signal at a first frequency using a first optical chopper, and modulating the reference signal at a second frequency differing from the first frequency using a second optical chopper. Modulating the sample and reference signals may also comprise providing a first circular row of apertures in the modulator to modulate the sample signal and providing a second circular row of apertures in the modulator to modulate the reference signal, wherein the number of apertures in the first circular row differs from the number of apertures in the second circular row.

According to certain embodiments, the method further comprises positioning the sample signal to contact the modulator at a first position and positioning the reference signal to contact the modulator at a second position, wherein the second position is separated from the first position by a desired phase shift angle. This method may also further comprise positioning a sample photodetector to detect the phase of the sample signal and positioning a reference photodetector to detect the phase of the reference signal. In many embodiments, modulating the sample and reference signals comprises digitally modulating the sample and reference signals. In certain embodiments, correcting drift in the detected sample signal comprises compensating for drift in the detected sample signal based on the value of the detected reference signal and an offset voltage generated by the electronics assembly.

In at least one embodiment, a method for analyzing a downhole fluid comprises transmitting a sample signal through a sample of the downhole fluid using a light source, transmitting a reference signal using the light source, and continuously measuring the reference signal to compensate for drift in the sample signal in real-time. This method may also further comprise communicating the measurements uphole to surface electronics.

According to certain embodiments, an apparatus for performing real-time analysis of a subterranean formation fluid comprises a light source, a reference signal continuously transmitted by the light source, a sample signal transmitted by the light source through a sample of the subterranean formation fluid, a modulator for modulating the sample and reference signals at different frequencies, at least one photodetector configured to continuously detect the sample and reference signals, and an electronics assembly configured to demodulate the sample signal and the reference signal and to compensate for drift in the detected sample signal in real-time based on the value of the detected reference signal.

Features from any of the above-mentioned embodiments may be used in combination with one another in accordance with the present invention. These and other embodiments, features and advantages will be more fully understood upon reading the following detailed description in conjunction with the accompanying drawings and claims.

BRIEF DESCRIPTION OF THE DRAWINGS

The accompanying drawings illustrate exemplary embodiments of the present invention and are a part of the specification. Together with the following description, the drawings demonstrate and explain the principles of the present invention.

FIG. 5A is a schematic diagram of an exemplary fluid analysis module employing a plurality of frequency modulators.

FIG. 5B is a front view of an exemplary frequency modulator configured for use in the fluid analysis module illustrated in FIG. 5A.

FIG. 7A is a schematic diagram of an exemplary fluid analysis module employing a single frequency modulator.

FIGS. 7B-7C are front views of exemplary frequency modulators configured for use in the fluid analysis module illustrated in FIG. 7A.

FIG. 8A is a chart illustrating the frequency spectrum of exemplary signals modulated by the modulators illustrated in FIGS. 7A-7C.

FIG. 8B is a chart of an exemplary waveform square modulated by the modulators illustrated in FIGS. 7A-7C.

FIG. 8C is a chart illustrating the frequency spectrum of exemplary signals square modulated by the modulators illustrated in FIGS. 7A-7C.

Figure 1A:
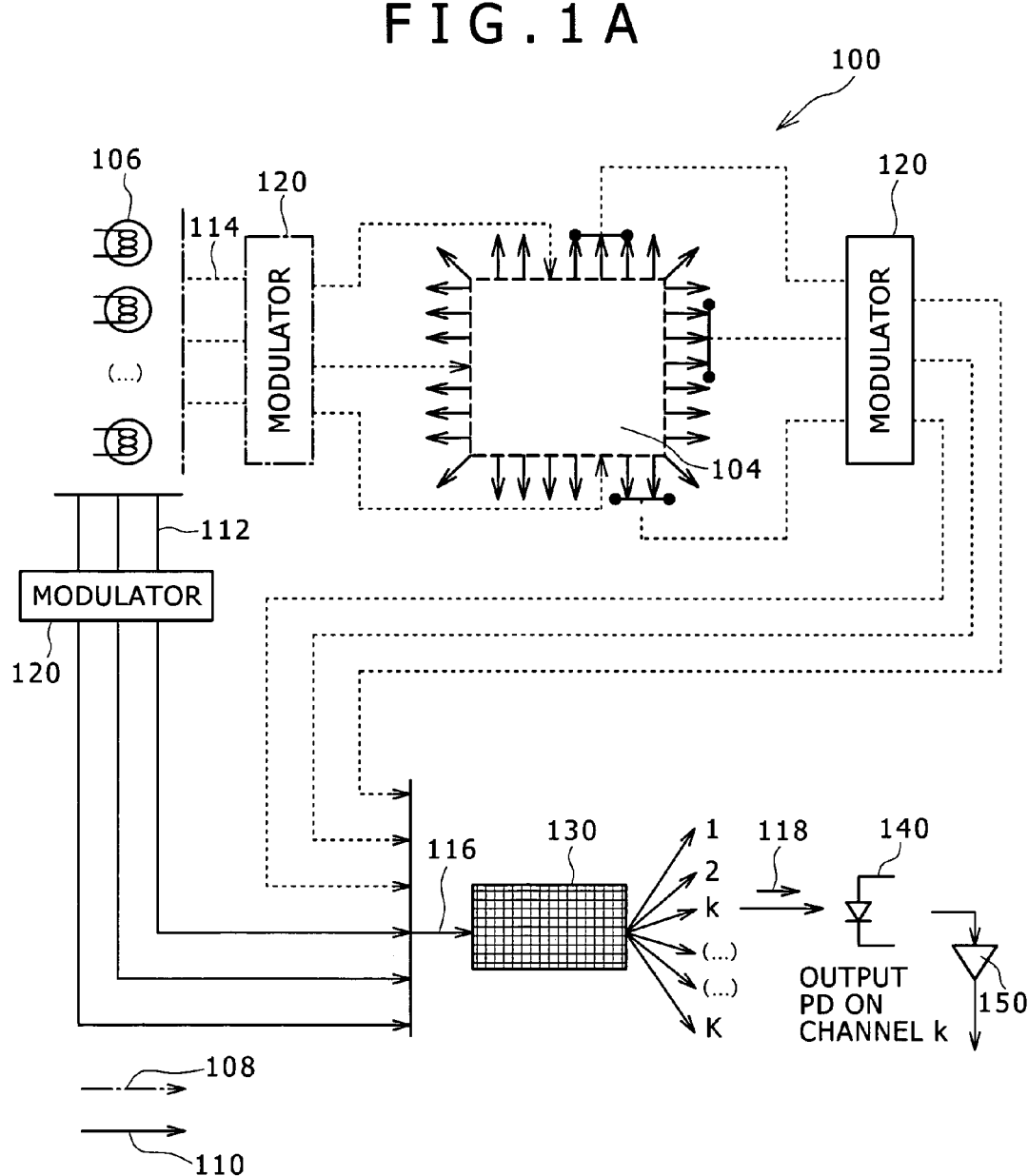
FIGS. 1A-1B are schematic diagrams of exemplary fluid analysis modules for analyzing extracted samples of formation fluids.

Throughout the drawings, identical reference characters and descriptions indicate similar, but not necessarily identical elements. While the present invention is susceptible to various modifications and alternative forms, specific embodiments have been shown by way of example in the drawings and will be described in detail herein. However, one of skill in the art will understand that the present invention is not intended to be limited to the particular forms disclosed. Rather, the invention covers all modifications, equivalents and alternatives falling within the scope of the invention as defined by the appended claims.

DETAILED DESCRIPTION OF EXEMPLARY EMBODIMENTS

Illustrative embodiments and aspects are described below. One of ordinary skill in the art will appreciate that in the development of any such embodiment, numerous implementation-specific decisions must be made to achieve the developers' specific goals, such as compliance with system-related and business-related constraints, which will vary from one implementation to another. Although such a development effort might be complex and time-consuming, the same would nevertheless be a routine undertaking for those of ordinary skill in the art having the benefit of this disclosure.

Figure 1B:
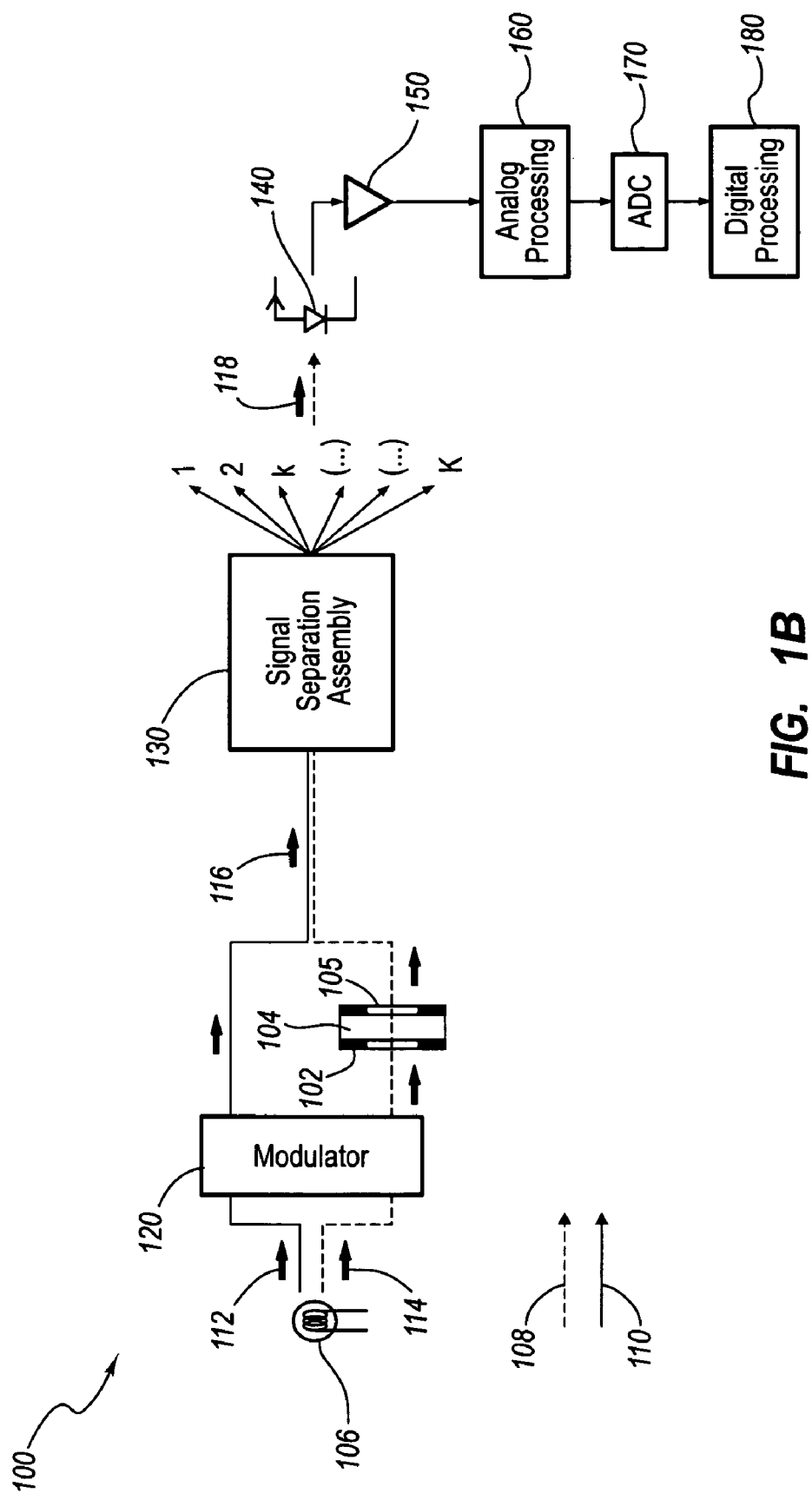
Figure 16:
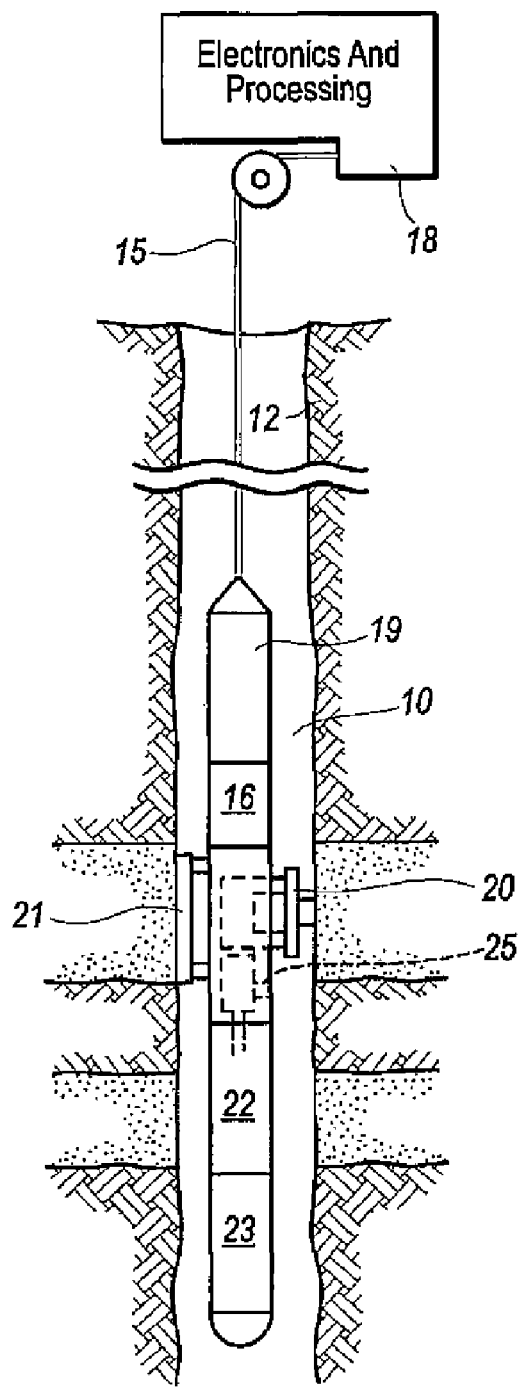
FIG. 16 illustrates an exemplary downhole tool in which a fluid analysis cell according to principles of the present invention may be implemented.

FIGS. 1A-1B are schematic diagrams of exemplary fluid analysis modules 100 for analyzing extracted samples of formation fluids. As will be appreciated by those of skill in the art, exemplary fluid analysis modules 100 may be adapted for use in a variety of environments and/or included in a number of different tools. For example, one or more fluid analysis modules 100 may form a portion of a fluid analysis module 25 housed in a downhole tool 10, as illustrated in FIG. 16. According to at least one embodiment, exemplary fluid analysis module 100 comprises a flowline 102 (FIG. 1B) housing an extracted formation fluid sample 104. Formation fluid sample 104 may be extracted, withdrawn, or admitted into flowline 102 in any number of ways known to those of skill in the art. For example, sample 104 may be admitted into flowline 102 by a fluid admitting/withdrawal assembly, such as fluid admitting/withdrawal assembly 20 illustrated in FIG. 16. As detailed above, fluid admitting/withdrawal assembly 20 may admit fluid samples by selectively sealing off or isolating portions of the wall of a borehole 12 (FIG. 16).

In certain embodiments, fluid analysis module 100 also comprises a light source 106 optically coupled via optical cabling (such as, for example, fiber optic cabling) to a reference signal path 110 and a sample signal path 108. Generally speaking, light source 106 represents any device or apparatus capable of transmitting light; including, for example, an incandescent lamp (such as a halogen lamp), a light-emitting diode (LED), a monochromator, or a tunable laser diode. In the exemplary embodiments illustrated in FIGS. 1A-1B, light source 106 transmits a reference signal 112 along reference signal path 110 and a sample signal 114 along sample signal path 108.

As seen in FIGS. 1A-1B, in at least one embodiment reference signal 112 and sample signal 114 are modulated by a modulator 120. Generally speaking, modulator 120 represents any form of mechanical or electrical device or apparatus capable of modulating a signal; including, for example, an optical chopper wheel, a signal generator, or the like. As discussed in greater detail below, modulator 120 may be configured to modulate one or more of the characteristics of signals 112 and 114; including, for example, the frequency, phase, or amplitude of the signals. Modulator 120 may also be configured to modulate signals 112, 114 using any number of analog or digital methods. In addition, modulator 120 may be positioned before or after flowline 102.

Figure 2:
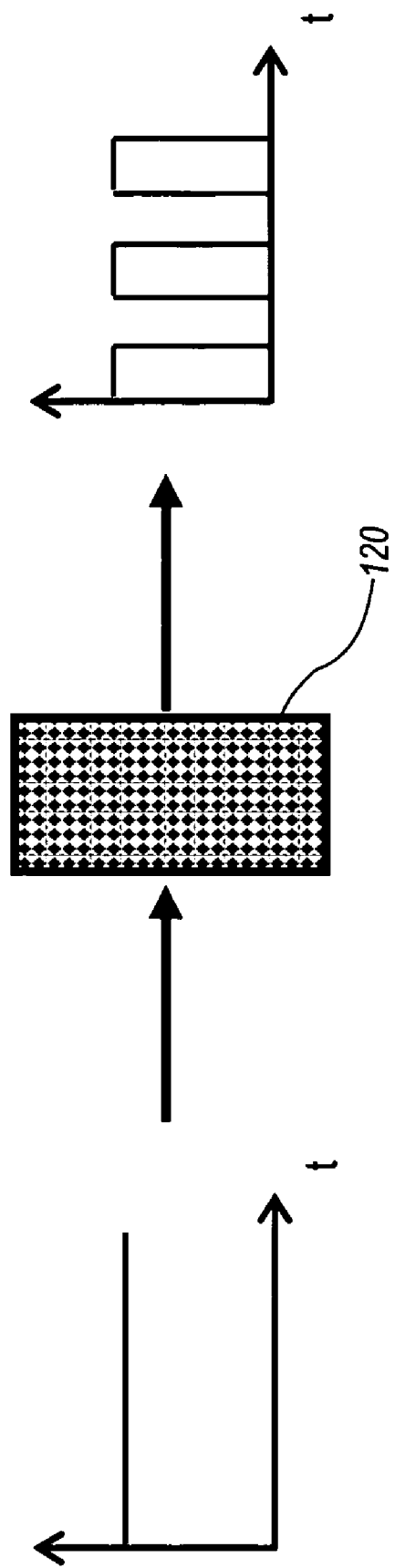
FIG. 2 is a diagram of exemplary input and output waveforms of a signal modulated by a signal modulator employed in the exemplary fluid analysis module of FIG. 1.

FIG. 2 is a diagram of exemplary input and output waveforms of a signal modulated by modulator 120. As seen in this figure, modulator 120 may alter the waveform of an input signal $I_{in}$ (such as reference signal 112 or sample signal 114) using frequency modulation. The resulting value of the input signal $I_{in}$ modulated by modulator 120 may be expressed as follows:

$$I_{in}(t) \times g_{mod}(t) = I_{out}(t) \quad (1)$$

where $I_{in}(t)$ is the value of the input signal as a function of time t, $g_{mod}(t)$ is a modulation function performed by modulator 120 as a function of time t, and $I_{out}(t)$ is the value of the signal output from modulator 120 as a function of time t. Although in this exemplary embodiment the input signal $I_{in}$ is illustrated as being modulated periodically by frequency, the modulation function $g_{mod}$ of modulator 120 may also be chosen to modulate various other characteristics of input signals; including, for example, the phase or amplitude of a signal.

In the exemplary embodiments illustrated in FIGS. 1A-1B, the spectral density of reference signal 112 and sample signal 114, after being modulated by modulator 120, may be expressed as follows:

$$I_{ref}(\lambda, t) = I_{source}(t) \times g_{ref}(t); \quad (2)$$

and $$I_{samp}(\lambda, t) = I_{source}(t) \times g_{samp}(t); \quad (3)$$

where $I_{ref}(\lambda,t)$ is the power spectral density of reference signal 112 as a function of wavelength and time, $I_{source}(t)$ is the spectral density of light source 106 as a function of time, $g_{ref}$ is a modulation function applied to reference signal 112 by modulator 120, $g_{samp}$ is a modulation function applied to sample signal 114 by modulator 120, and $I_{samp}(\lambda,t)$ is the power spectral density of sample signal 114 as a function of wavelength and time.

As seen in FIGS. 1A-1B, reference signal 112 may be directly transmitted towards a signal separation assembly 130 after being modulated by modulator 120. Sample signal 114, on the other hand, may be directed onto a sample window 105 (FIG. 1B) of flowline 102 after being modulated by modulator 120. Sample signal 114 may then be transmitted through sample window 105, across fluid sample 104, and through a second sample window 105. In general, sample windows 105 may be formed of any substantially transparent material configured to allow a signal to be transmitted therethrough; including, for example, sapphire, glass, and the like. As sample signal 114 passes through sample 104, one or more of the properties of sample signal 114 are changed. For example, sample 104 may absorb (through, for example, absorption spectroscopy), reemit (through, for example, fluorescence), or wavelength shift (through, for example, non-linear interaction such as Raman Spectroscopy) all or a portion of sample signal 114. In this, the sample signal 114 may be spectrally analyzed after interaction with sample 104 to determine fluid properties of the sample 104.

The present invention further contemplates real time calibration of spectral characteristics of the light source 106 to compensate for drift in the detected signals, such as excitation signals after absorption and light emitted by the sample 104 after excitation. Upon passing through flowline 102, sample signal 114 may be combined with reference signal 112 to form a combined signal 116 input into signal separation assembly 130 with signal 118 being the output signal(s) from signal separation assembly 130.

In general, signal separation assembly 130 represents any device or apparatus capable of separating one or more signals into the respective wavelengths making up the signal. For example, signal separation assembly 130 may be a spectrometer (such as a grating spectrometer), a filter array, or other similar device or apparatus. In certain embodiments, a fixed wavelength spectrometer may be provided with a plurality of output channels, each corresponding to a spectral area of interest. In this embodiment, each channel may be characterized by a channel transfer function $f_k(\lambda)$ that defines the channel spectral filtering. Usually, this function has a bell-like shape and may be characterized by a central wavelength and a half-width maximum (HWM) that defines the spectrometer's optical resolution.

Figure 15A:
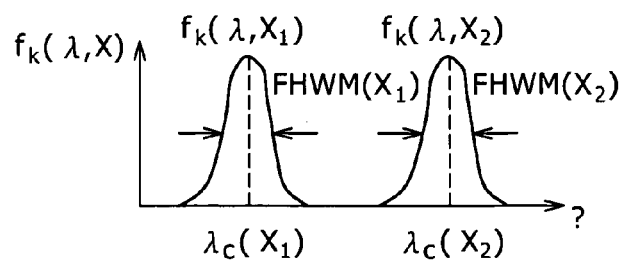
FIG. 15A depicts a relationship between a channel transfer function and an external command signal for a tunable spectrometer.
Figure 15B:
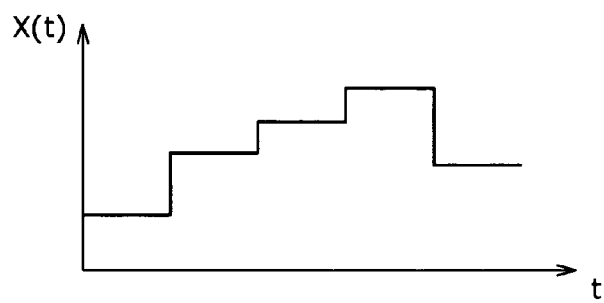
FIG. 15B illustrates a stepping function for a tunable spectrometer wherein X(t) is defined by the interval it is kept constant.
Figure 15C:
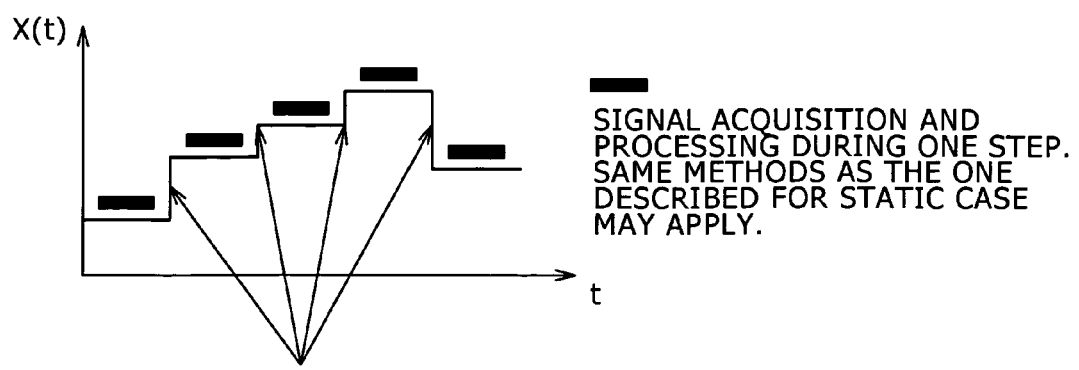
FIG. 15C depicts a signal processing sequence in the case of a stepping control function for a tunable spectrometer.

In certain embodiments, a tunable spectrometer may be provided as the signal separation assembly 130, described below in connection with FIGS. 15A-C.

In the exemplary embodiments illustrated in FIGS. 1A-1B, signal separation assembly 130 serves to separate combined signal 116 (comprising the spectral contributions of reference signal 112 and sample signal 114) into one or more channels k of varying wavelengths. For example, signal separation assembly 130 may separate combined signal 116 into a first channel $k_1$ of a first wavelength, a second channel $k_2$ of a second wavelength, a third channel $k_3$ of a third wavelength, a fourth channel $k_n$ of a wavelength n, and so on. In at least one embodiment, the power spectral density of the signal output at each channel k (as a function of its wavelength) may be expressed by the following relationship:

$$S_k(\lambda) = I_{combined}(\lambda, t) \times f_k(\lambda); \quad (4)$$

where $S_k(\lambda)$ is the power spectral density of the signal at channel k as a function of wavelength, $I_{combined}(\lambda,t)$ is the power spectral density of the signal entering signal separation assembly 130 (in this case, combined signal 116) as a function of time and wavelength, and $f_k(\lambda)$ is the optical filtering function performed by signal separation assembly 130 on channel k as a function of wavelength. Generally speaking, $I_{combined}$ represents the combined signals of reference signal 112 and sample 114, expressed as follows:

$$I_{combined}(\lambda, t) = I_{ref}(\lambda, t) + I_{samp}(\lambda, t); \quad (5)$$

where $I_{ref}(\lambda,t)$ is the power spectral density of reference signal 112 as a function of wavelength and time, and $I_{samp}(\lambda,t)$ is the power spectral density of sample signal 114 as a function of wavelength and time.

In certain embodiments, signal separation assembly 130 directs the spectrally separated channels k (output signals 118 in FIGS. 1A-1B) of combined signal 116 onto one or more photodetectors 140. Photodetectors 140 may be formed generally of any suitable semiconducting material capable of detecting light signals. For example, photodetectors 140 may be Indium-Gallium-Arsenide (InGaAs) photodiodes or Silicon (Si) photodiodes. Photodetectors 140 may operate in either a photovoltaic mode or a photoconductive mode to convert the optical signal input therein into voltage or current, respectively. In at least one embodiment, photodetectors 140 operate in photoconductive mode to convert the inputted optical signals into current. The current generated at the output of each photodetector 140 may be expressed as follows:

$$(i_L)_k = \int I_{combined}(\lambda) G_k(\lambda) f_k(\lambda) d\lambda; \quad (6)$$

where $(i_L)_k$ is the current value at the output of each photodetector 140 and $G_k$ is the optical gain at the output of photodetector 140 as a function of wavelength. More particularly, at a pixel level the current at the output of each photodetector 140 may be expressed as follows:

$$(i_L)k = (i_L)_{k,samp} + (i_L)_{k,ref}; \quad (7)$$

$$\text{with } (i_L)_{k,samp} = \int I_{samp}(\lambda) G_k(\lambda) f_k(\lambda) d\lambda; \quad (8)$$

$$\text{and } (i_L)_{k,ref} = \int I_{ref}(\lambda) G_k(\lambda) f_k(\lambda) d\lambda; \quad (9)$$

where $(i_L)_{k,ref}$ is the contribution of reference signal 112 to $(i_L)_k$, and $(i_L)_{k,samp}$ is the contribution of sample signal 114 to $(i_L)_k$. When the modulation function of modulator 120 is included, then the current at the output of each photodetector 140 may be expressed as follows:

$$(i_L)_k(t) = (i_L)_{k,samp} \times g_{samp}(t) + (i_L)_{k,ref} \times g_{ref}(t); \quad (10)$$

with $g_{ref}$ representing the modulation function applied to reference signal 112 by modulator 120, and $g_{samp}$ representing the modulation function applied to sample signal 114 by modulator 120.

In the exemplary embodiments illustrated in FIGS. 1A-1B, the output of photodetector 140 may be connected to the input of an analog signal conditioner 150. Generally speaking, analog signal conditioner 150 represents any form of electrical or mechanical device capable of converting one type of electronic signal into another type of signal. In certain embodiments, analog signal conditioner 150 represents a transimpedance amplifier for converting the current generated by photodetector 140 into voltage, in a manner well known to those of skill in the art. As seen in the exemplary embodiment illustrated in FIG. 1B, the output of analog signal conditioner 150 may be connected to the input of an analog processor 160. Generally speaking, analog processor 160 represents any form of device or apparatus capable of processing analog signals. Analog processor 160 may be configured to perform a variety of functions; including, for example, compression, ratioing, background subtraction, or other such functions.

According to at least one embodiment, the output of analog processor 160 is connected to the input of an analog-to-digital (A/D) converter 170, which may be formed of any circuit or device capable of converting an analog signal to a digital one. In the exemplary embodiment illustrated in FIG. 1B, A/D converter 170 may convert the analog signal transmitted from analog processor 160 into a digital signal and supply the converted signal to a digital processor 180. Generally speaking, digital processor 180 represents any form of apparatus or device capable of digitally processing signals; including, for example, a microprocessor in a computer. In at least one embodiment, digital processor 180 estimates the optical density of fluid sample 104 based on the various inputs supplied by A/D converter 170. Specifically, digital processor 180 may estimate the optical density of fluid sample 104 in accordance with the following equation:

$$(OD_k)_{est} = \log \frac{\int I_{samp}(\lambda) G_k(\lambda) f_k(\lambda) d\lambda}{\int I_{ref}(\lambda) G_k(\lambda) f_k(\lambda) d\lambda}; \quad (11)$$

where $(OD_k)_{est}$ represents an estimate of the optical density of fluid sample 104. For ease of use, elements 150, 160, 170, and 180 may be referred to herein as an "electronics assembly."

Accordingly, based on the values supplied by photodetector 140 (and in particular the known values of $g_{ref}$ and $g_{samp}$, which are used in computing the values of $I_{ref}$ and $I_{samp}$, respectively, in Eq. 11) digital processor 180 may compute the estimated optical density of fluid sample 104. As is known to those of skill in the art, this computed optical density enables a user to determine the presence and/or amount of various chemical compositions in fluid sample 104, thereby enabling the user to effectively analyze the formation fluid. Advantageously, by (1) continuously supplying reference signal 112 and sample signal 114, (2) modulating these signals, and (3) separating these signals using a digital processor in this exemplary manner, fluid analysis module 100 effectively compensates, in real-time, for drift in the light sources, photodetectors, and processing electronics used in analyzing formation fluids. Changes in temperature in a borehole and/or the tools lowered into such a borehole are thus accounted for in real-time, thereby increasing the overall accuracy and reliability of the fluid analysis module and eliminating the need for conventional calibration methods and techniques.

Although many configurations and modifications of exemplary fluid analysis module 100 are possible, various exemplary embodiments and configurations of this fluid analysis module, and in particular modulator 120, will now be described with reference to the appropriate figures.

Figure 3:
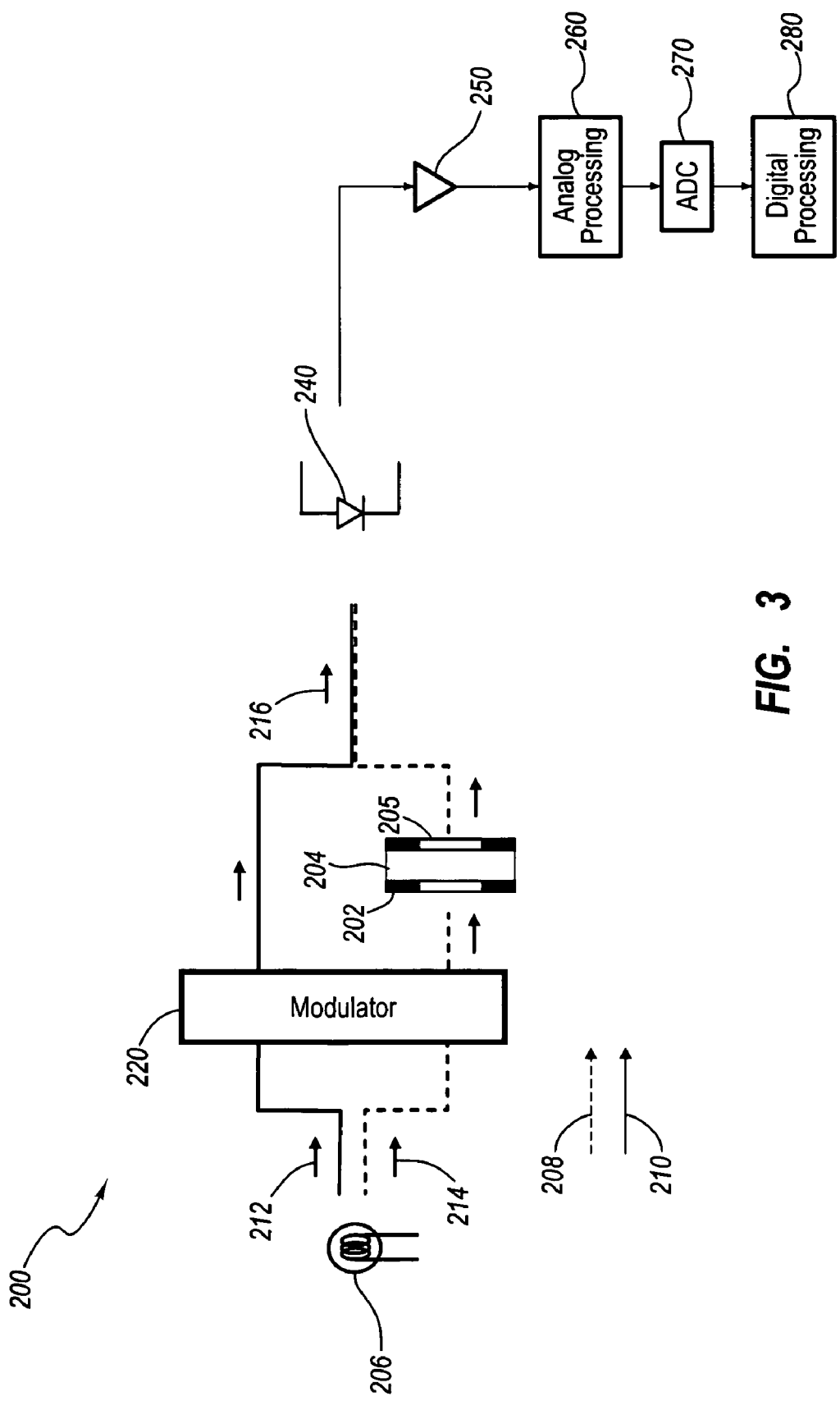
FIG. 3 is a schematic diagram of an exemplary fluid analysis module employing a tunable light source.

FIG. 3 is a schematic diagram of an exemplary fluid analysis module 200 employing a tunable light source 206. According to at least one embodiment, the exemplary fluid analysis module illustrated in this figure comprises a flowline 202 housing an extracted formation fluid sample 204. Tunable light source 206 may be optically coupled via optical cabling to a reference signal path 210 and a sample signal path 208. In this exemplary embodiment, tunable light source 206 transmits a reference signal 212 along reference signal path 210 and a sample signal 214 along sample signal path 208.

Generally speaking, tunable light source 206 represents any form of device or apparatus capable of generating light at a specified wavelength; including, for example, a monochromator or a tunable laser diode. In at least one embodiment, the wavelength of light generated by tunable light source 206 may be varied as needed to test the chemical composition of fluid sample 204. As seen in FIG. 3, a fluid analysis module employing tunable light source 206 employs many of the same components used in exemplary fluid analysis module 100. However, since the wavelength of light generated by tunable light source 206 may be varied as desired, the need for a signal separation assembly (such as signal separation assembly 130 in FIGS. 1A-1B) positioned prior to photodetector 240 is effectively eliminated. Thus, in at least one embodiment, a fluid analysis module (such as the fluid analysis module illustrated in FIG. 3) employs a tunable light source 206 instead of a standard light source and signal separation assembly.

Figure 4:
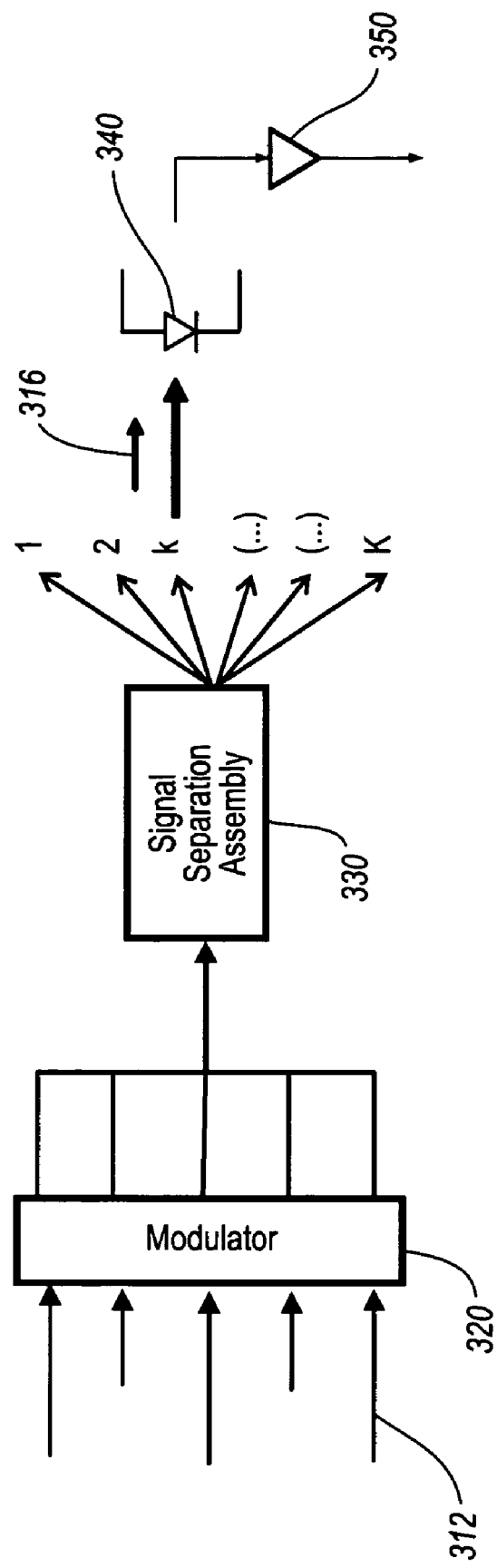
FIG. 4 is a schematic diagram of an exemplary fluid analysis module employing a plurality of signal paths.

FIG. 4 is a schematic diagram of an exemplary fluid analysis module employing a plurality of signal paths. In at least one embodiment, the fluid analysis module in this figure comprises a plurality of signal paths 312 connected in parallel to a modulator 320. Generally speaking, one or more of signal paths 312 may serve as reference paths (such as reference signal path 110 in FIGS. 1A-1B) or sample paths (such as sample signal path 108 in FIGS. 1A-1B) for a fluid analysis module. Specifically, one or more of signal paths 312 may be configured to direct light from a light source through a sample window and across a fluid sample prior to entering signal separating assembly 330 (such as sample signal path 108 in FIGS. 1A-1B). Alternatively or in combination therewith, one or more of signal paths 312 may be configured to direct light from a light source directly to a signal separation assembly 330 (such as reference signal path 10 in FIGS. 1A-1B).

By providing a plurality of signal paths 312 in this manner, various differing measurements of a fluid sample (such as fluid sample 104 in FIGS. 1A-1B) may be obtained simultaneously. For example, various wavelengths and intensities of light may be simultaneously transmitted through a fluid sample in order to simultaneously determine the presence or absence of a number of differing chemical compounds. Alternatively, the wavelengths and intensities of the light transmitted through one or more signal paths 312 may be equal to one another for redundancy purposes to account and/or compensate for variations in component accuracy. Accordingly, the arrangement of the plurality of signal paths 312 in the exemplary fluid analysis cell in FIG. 4 may advantageously result in various increases in efficiency and accuracy.

FIG. 5A is a schematic diagram of an exemplary fluid analysis module 400 employing a plurality of frequency modulators. According to at least one embodiment, the exemplary fluid analysis module illustrated in this figure comprises a flowline 402 housing an extracted formation fluid sample 404. A light source 406 may be optically coupled via optical cabling to a reference signal path 410 and a sample signal path 408. In this exemplary embodiment, light source 406 transmits a reference signal 412 along reference signal path 410 and a sample signal 414 along sample signal path 408.

As seen in FIGS. 5A-5B, in at least one embodiment reference signal 412 and sample signal 414 are directed onto a first optical chopper wheel 420 and a second optical chopper wheel 425, respectively. As illustrated in FIG. 5B, in certain embodiments chopper wheels 420, 425 comprise a plurality of apertures 422 periodically spaced along the circumference of the chopper wheel. In many embodiments, chopper wheels 420, 425 are connected to a motor (not illustrated) configured to rotate the circular blade of the chopper wheel at a specified frequency $f_{motor}$. As chopper wheels 420, 425 rotate at this specified frequency, signals 412, 414 periodically pass through apertures 422 in chopper wheels 420, 425 towards signal separation assembly 430. By periodically allowing signals 412, 414 to pass through chopper wheels 420, 425 in this manner, chopper wheels 420, 425 effectively modulate reference signal 412 and sample signal 414. The frequency at which these signals 412, 414 are modulated may be expressed as follows:

$$f_{mod} = N_{apert} \times f_{motor} \quad (12)$$

where $f_{mod}$ is the modulation frequency, $N_{apert}$ is the number of apertures in the chopper wheel, and $f_{motor}$ is the rotation frequency of the motor.

In at least one embodiment, chopper wheels 420, 425 are configured such that the modulation frequency of reference signal 412 ($f_{mod,ref}$) differs from the modulation frequency of sample signal 414 ($f_{mod,sample}$). This may be accomplished in a number of ways; including, for example, by rotating first chopper wheel 420 at a different speed from the rotation speed of second chopper wheel 425, or by configuring first chopper wheel 420 to have a different number of apertures 422 than the number used in second chopper wheel 425.

Figure 6:
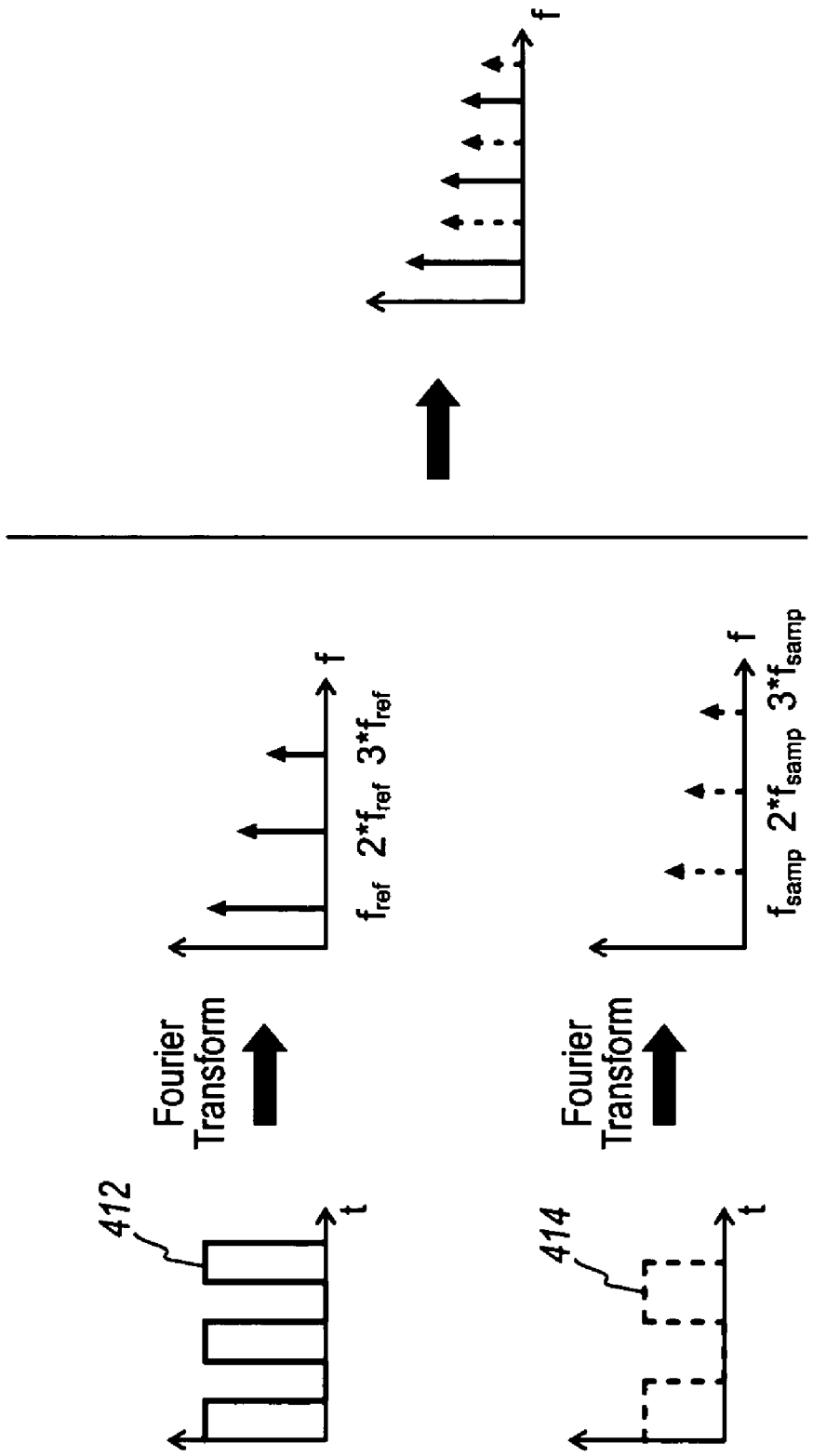
FIG. 6 is an exemplary chart of the discrete and combined waveforms modulated by the modulators illustrated in FIGS. 5A-5B.

In certain embodiments, modulating reference signal 412 and sample signal 414 at different frequencies in this manner facilitates the estimation of the amplitudes of $(i_L)_{k,samp}$ and $(i_L)_{k,ref}$, which, as detailed in Eq. 7, above, constitute the discrete contributions made by sample signal 414 and reference signal 412 to the current value at the output of photodetector 440 ($(i_L)_k$). For example, as seen in FIG. 6, an estimation of the amplitudes of the harmonics of reference signal 412 and sample signal 414 may be computed using known harmonics techniques and tools (such as, for example, Fourier analysis techniques, lock-in analysis techniques, or the like) since the harmonics of each of these signals are proportional to their respective contributions to the current output at photodetector 440. Specifically, since each of the harmonics of the modulated reference signal 412 are proportional to the amplitude of this signal's contribution to the output at photodetector 440 (namely, $\int I_{ref}(\lambda) G_k(\lambda) f_k(\lambda) d\lambda$), while the harmonics of the modulated sample signal 414 are proportional to the amplitude of this signal's contribution to the output at photodetector 440 (namely, $\int I_{samp}(\lambda) G_k(\lambda) f_k(\lambda) d\lambda$), the optical density of fluid sample 404 may be estimated using Eq. 11, detailed above.

As seen in FIG. 5A, reference signal 412 may be directly transmitted towards a signal separation assembly 430 after being modulated by chopper wheel 420. Sample signal 414, on the other hand, may be directed onto a sample window 405 of flowline 402 after being modulated by chopper wheel 425. Sample signal 414 may then be transmitted through sample window 405, across fluid sample 404, and through a second sample window 405. Upon passing through flowline 402, sample signal 414 may be combined with reference signal 412 to form a combined signal 416 input into signal separation assembly 430. In certain embodiments, signal separation assembly 430 directs the spectrally separated channels k of combined signal 416 onto one or more photodetectors 440. In the exemplary embodiment illustrated in FIG. 5A, the output of photodetector 440 may be connected to the input of an analog signal conditioner 450. The output of analog signal conditioner 450 may be connected to the input of an analog processor 460. According to at least one embodiment, the output of analog processor 460 is connected to the input of an analog-to-digital (A/D) converter 470. In the exemplary embodiment illustrated in FIG. 5A, A/D converter 470 may convert the analog signal transmitted from analog processor 460 into a digital signal and supply the converted signal to a digital processor 480.

Advantageously, because the fluid analysis module according to this exemplary embodiment uses a detection method that only employs alternating current (AC), the various voltage offsets of the electronic components in the module need not be measured or accounted for. More particularly, because voltage offsets are generally only generated when using direct current (DC), this exemplary fluid analysis module's use of AC eliminates the requirement that voltage offsets be measured and accounted for. For example, when a light source in this embodiment is switched off, no AC signal is generated on the detecting photodetector, such that the conventional voltage offset calculations need not be used.

FIG. 7A is a schematic diagram of an exemplary fluid analysis module 500 employing a single frequency modulator. According to at least one embodiment, the exemplary fluid analysis module illustrated in this figure comprises a flowline 502 housing an extracted formation fluid sample 504. A light source 506 may be optically coupled via optical cabling to a reference signal path 510 and a sample signal path 508. In this exemplary embodiment, light source 506 transmits a reference signal 512 along reference signal path 510 and a sample signal 514 along sample signal path 508.

As seen in FIGS. 7A-7C, in at least one embodiment reference signal 512 and sample signal 514 are directed onto a single optical chopper wheel 520. As illustrated in FIGS. 7B-7C, in certain embodiments chopper wheel 520 comprises a first row of apertures 522 periodically spaced along the circumference of the chopper wheel, and a second row of apertures 524 periodically spaced within the first row of apertures 522. In many embodiments, the number of apertures employed in first row 522 is different from the number of apertures employed in second row 524. Although in the exemplary embodiments illustrated in FIGS. 7B-7C the number of apertures in second row 524 is greater than the number of apertures employed in first row 522, this configuration may be reversed such that the number of apertures in first row 522 is greater than the number employed in second row 524. In certain embodiments, chopper wheel 520 and reference signal path 510 may be configured and positioned such that reference signal 512 transmits directly onto second row 524 (as indicated by dot 528). In addition, chopper wheel 520 and sample signal path 508 may be configured and positioned such that sample signal 514 transmits directly onto first row 522 (as indicated by dot 526). As with chopper wheels 420, 425, chopper wheel 520 may be connected to a motor (not illustrated) configured to rotate the circular blade of the chopper wheel at a specified frequency.

By configuring first and second rows 522, 524 in this manner, chopper wheel 520 may modulate reference signal 512 using a modulation frequency that is different from the frequency at which sample signal 514 is modulated. Unfortunately, as is illustrated in FIG. 8A, because these two modulation frequencies (namely, the modulation frequency of reference signal 512 and the modulation frequency of sample signal 514) are generated by the same chopper wheel (chopper wheel 520), these modulation frequencies are multiples of one another. This results in a frequency spectrum that, when analyzed using Fourier analysis or the like, contains frequency components that may not be singly attributable to either signal 512, 514, but instead include contributions from each signal. For example, as illustrated in FIG. 8A, the $2f_0$ harmonic contains contributions from both reference signal 512 and sample signal 514 (as represented by combined signals 515). Due to these shared harmonics, separating the contributions made by reference signal 512 from sample signal 514, and ultimately estimating the optical density of fluid sample 504 based on these values, may prove difficult based on this method of analysis alone.

Thus, in accordance with at least one embodiment, the modulation functions $g_{mod,samp}(t)$ and $g_{mod,ref}(t)$ are chosen such that in the frequency domain, certain harmonic multiples have an amplitude equal to zero. For example, as illustrated in FIGS. 8B-8C, reference signal 512 may be modulated by chopper wheel 520 using square modulation at a 50% duty cycle, thereby eliminating all even number harmonics. The modulation frequency of sample signal 514 may then be chosen to be equal to double that of the modulation frequency of the reference signal 512. The contribution of the two signals 512, 514 may then be separated using known harmonic analysis techniques, as illustrated by separated signals 517 in the frequency domain in FIG. 8C, and as discussed in greater detail above.

Figure 9A:
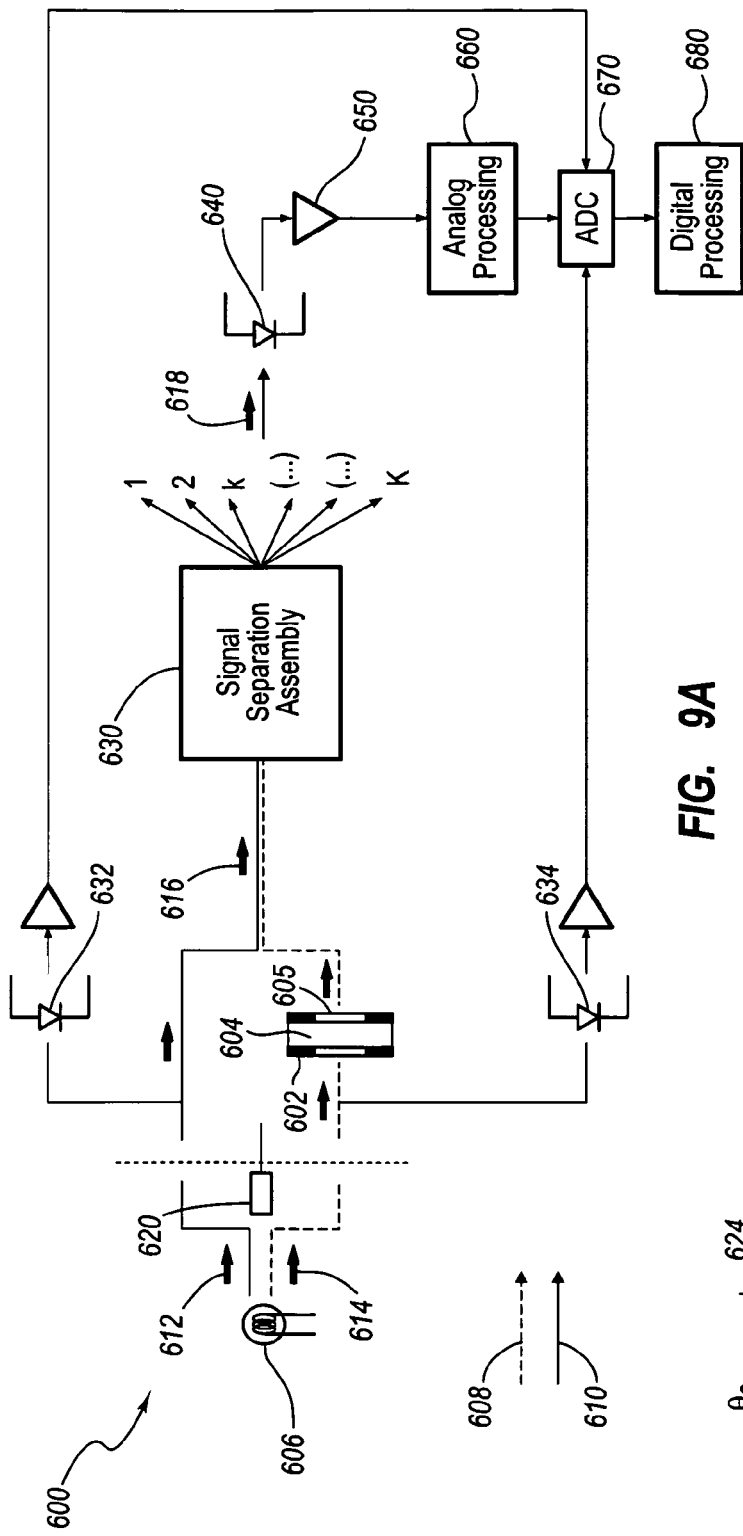
FIG. 9A is a schematic diagram of an exemplary fluid analysis module employing a phase-shift modulator.

FIG. 9A is a schematic diagram of an exemplary fluid analysis module 600 employing a phase-shift modulator. According to at least one embodiment, the exemplary fluid analysis module illustrated in this figure comprises a flowline 602 housing an extracted formation fluid sample 604. A light source 606 may be optically coupled via optical cabling to a reference signal path 610 and a sample signal path 608. In this exemplary embodiment, light source 606 transmits a reference signal 612 along reference signal path 610 and a sample signal 614 along sample signal path 608. In certain embodiments, a sample photodiode 634 may be placed along sample signal path 608 to measure the phase of sample signal 614. Similarly, a reference photodiode 632 may be placed along reference signal path 610 to measure the phase of reference signal 612. As with photodetectors 140, photodetectors 632, 634 may be formed generally of any suitable semiconducting material capable of detecting light signals; including, for example, Indium-Gallium-Arsenide (InGaAs) or Silicon (Si).

Figure 9B:
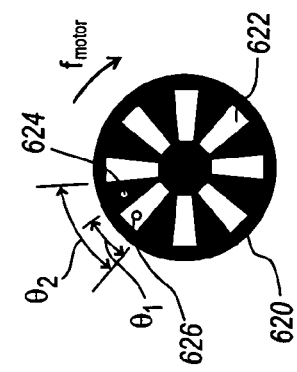
FIG. 9B is a front view of an exemplary phase-shift modulator configured for use in the exemplary fluid analysis module illustrated in FIG. 9A.

As seen in FIGS. 9A-9B, in at least one embodiment reference signal 612 and sample signal 614 are directed onto a single optical chopper wheel 620. As illustrated in FIG. 9B, chopper wheel 620 may comprise a plurality of apertures 622 periodically spaced along the circumference of the chopper wheel. In certain embodiments, chopper wheel 620 and reference signal path 610 may be configured and positioned such that reference signal 612 contacts chopper wheel 620 at a first position 624, while sample signal 614 contacts chopper wheel 620 at a second position 626. In the exemplary embodiment illustrated in FIG. 9B, the angular distance between second position 626 and first position 624 is represented by a first angle $\theta_1$, while the angular distance between the edges of adjacent apertures 622 is represented by a second angle $\theta_2$. The phase shift between reference signal 612 and sample signal 614 may then be expressed as follows:

$$\varphi = 2\pi \frac{\theta_1}{\theta_2}; \tag{13}$$

where $\phi$ represents the phase shift between signals 612 and 614.

Figure 10:
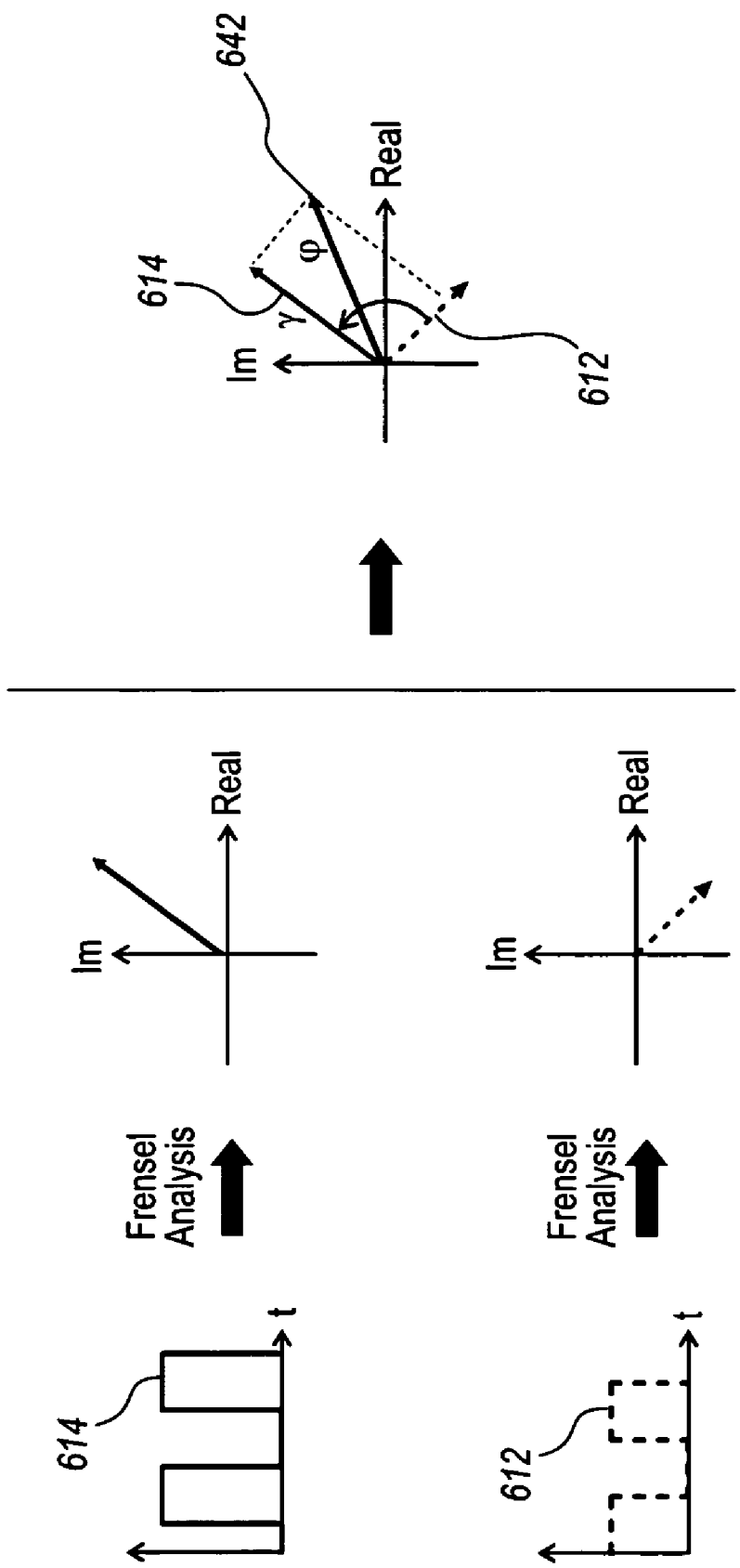
FIG. 10 is an illustration of the phases of exemplary signals modulated by the phase-shift modulators illustrated in FIGS. 9A-9B.

An exemplary illustration of the behavior of the phases of signals 612, 614 from FIG. 9A is provided in the Frensel diagram of FIG. 10. In at least one embodiment, the waveforms and phases of signals 612 and 614 illustrated in this figure are measured using the sample photodiode 634 placed along sample signal path 608 and the reference photodiode 632 (FIG. 9A) placed along reference signal path 610 (FIG. 9A), although other configurations and measuring devices may be possible. As seen in the combined Frensel diagram of FIG. 10, an output phase signal 642 output at photodetector 640 (FIG. 9A) generally represents the sum of the contributions from reference signal 612 and sample signal 614, which are phase shifted from one another by chopper wheel 620 (FIG. 9A).

Figure 11:
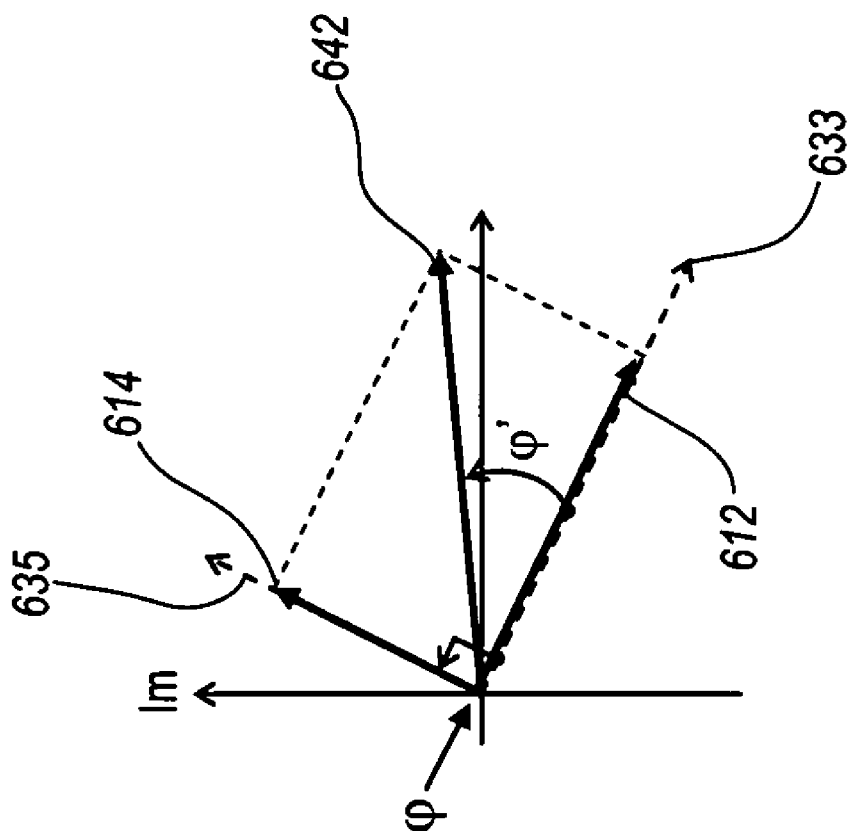
FIG. 11 is an illustration of the phases of exemplary signals modulated by the phase-shift modulators illustrated in FIGS. 9A-9B, when the difference between the modulated signals is equal to 90°.

A more detailed Frensel diagram is provided in FIG. 11. Generally speaking, this figure illustrates the phases of reference signal 612, sample signal 614, a reference phase signal 633 (detected by reference photodiode 632 in FIG. 9A), a sample phase signal 635 (detected by sample photodiode 634 in FIG. 9A), and output phase signal 642 (output by photodiode 640 in FIG. 9A). As seen in this figure, output phase 642 generally represents the sum of the contributions from reference signal 612 and sample signal 614. In at least one embodiment, when the phase difference $\phi$ between signals 612 and 614 is equal to 90°, the phase shift between reference phase signal 633 and output phase signal 642 is equal to $\phi'$, Generally speaking, the value of $\phi'$ may be expressed as follows:

$$\tan\varphi' = \frac{\int I_{samp}(\lambda) G_k(\lambda) f_k(\lambda) d\lambda}{\int I_{ref}(\lambda) G_k(\lambda) f_k(\lambda) d\lambda}. \tag{14}$$

The phase shift difference $\phi'$ illustrated in FIG. 11 may be measured using any number of methods. For example, signals 633 and 642 may be digitized and processed using Fourier analysis, digital lock-in amplifiers, or the like. Once the values of signals 633 and 642 have been digitized and measured, the value of $\phi'$ may then be computed using Eq. 14. Advantageously, once the value of $\phi'$ has been determined, the optical density of sample 604 (FIG. 9A) may then also be estimated using the following equation:

$$(OD_k)_{est} = \log(\tan(\phi')) \qquad (15)$$

Figure 12:
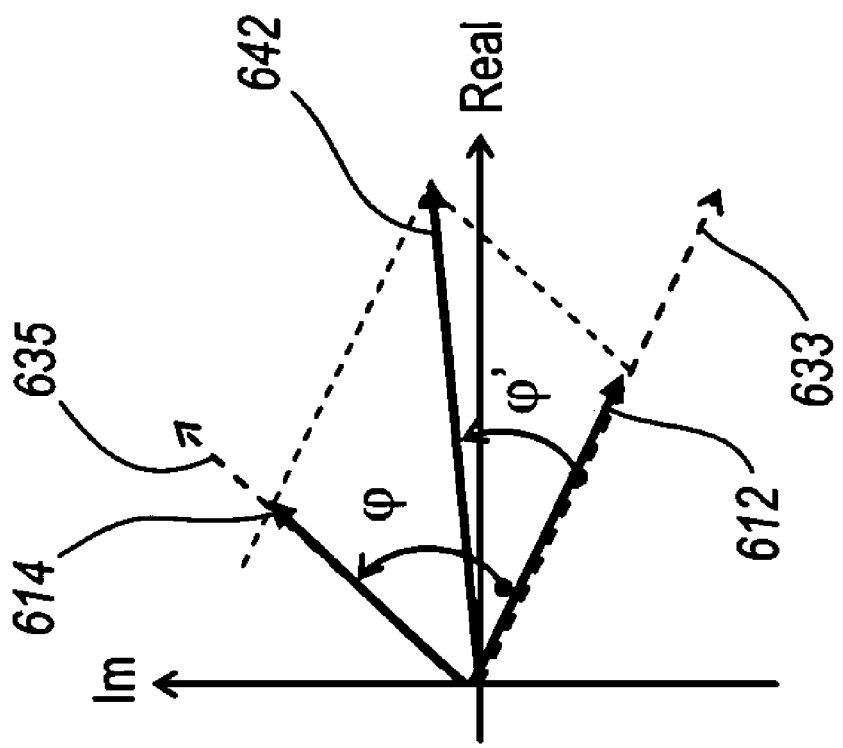
FIG. 12 is an illustration of the phases of exemplary signals modulated by the phase-shift modulators illustrated in FIGS. 9A-9B, when the difference between the modulated signals is not equal to 90°.

FIG. 12 is an illustration of the phases of signals 612 and 614 when the difference between these signals is not equal to 90°. As seen in this figure, output phase signal 642 generally represents the sum of the contributions from reference signal 612 and sample signal 614, which are phase shifted from one another by chopper wheel 620 (FIG. 9A). Generally speaking, this figure illustrates the phases of reference signal 612, sample signal 614, reference phase signal 633 (detected by reference photodiode 632 in FIG. 9A), sample phase signal 635 (detected by sample photodiode 634 in FIG. 9A), and output phase signal 642 (output by photodiode 640 in FIG. 9A). In at least one embodiment, when the phase difference $\phi$ between signals 612 and 614 is not equal to 90°, the value of $\phi'$ may be expressed as follows:

$$\frac{\int I_{ref}(\lambda) G_k(\lambda) f_k(\lambda) d\lambda}{\int I_{samp}(\lambda) G_k(\lambda) f_k(\lambda) d\lambda} = \frac{\sin\varphi}{\tan\varphi'} - \cos\varphi. \qquad (16)$$

As with the situation illustrated in FIG. 11, this phase shift difference $\phi'$ may be measured using any number of methods. For example, signals 633, 635, and 642 may be digitized and processed using Fourier analysis, digital lock-in amplifiers, or the like. Once the values of signals 633, 635, and 642 have been digitized and measured, the value of $\phi'$ may then be computed using Eq. 16. Advantageously, once the value of $\phi'$ has been determined, the optical density of sample 604 may then be estimated using the following equation:

$$(OD_k)_{est} = -\log\left(\frac{\sin\varphi}{\tan\varphi'} - \cos\varphi\right) \qquad (17)$$

Figure 13B:
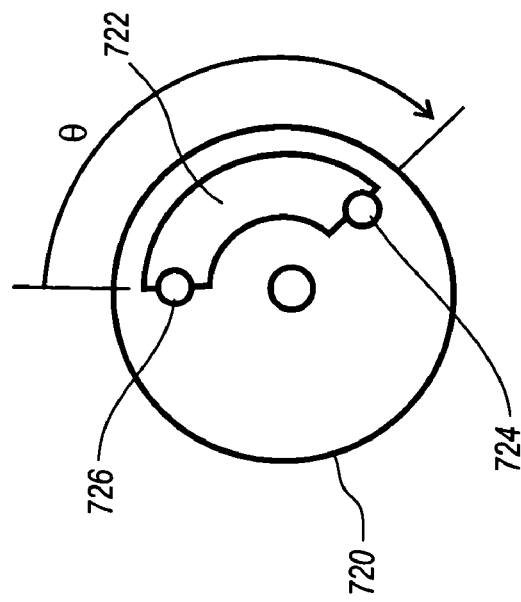
FIG. 13B illustrates an alternative embodiment of a phase-shift modulator configured for use in the exemplary fluid analysis module illustrated in FIG. 9A.
Figure 13A:
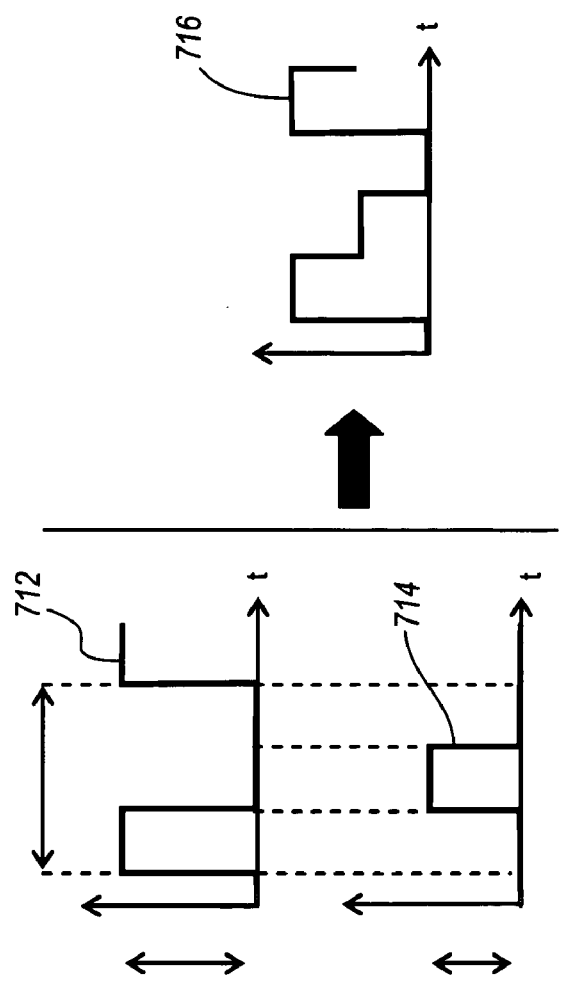
FIG. 13A is an illustration of an exemplary input waveform generated by the phase-shift modulator illustrated in FIG. 13B.

FIGS. 13A-13B illustrate an alternative embodiment of a phase-shift modulator (and its input waveform) configured for use in the exemplary fluid analysis module illustrated in FIG. 9A. As seen in FIG. 13B, a single optical chopper wheel 720 generally consists of a single aperture 722 formed within a substantial portion of the circumference of the chopper wheel. In certain embodiments, chopper wheel 720 is positioned such that a reference signal 712 transmitted along a reference signal path contacts chopper wheel 720 at a first position 724, while a sample signal 714 transmitted along a sample signal path contacts chopper wheel 720 at a second position 726. In the exemplary embodiment illustrated in FIG. 13B, the temporal and angular distance between second position 726 and first position 724 is represented by an angle $\theta$. In at least one embodiment, at least a portion of first and second positions 724, 726 fall within aperture 722. While angle $\theta$ may be equal to any number of angles, in at least one embodiment angle $\theta$ equals 120°.

Generally speaking, chopper wheel 720 and aperture 722 may be used to sequentially mask a reference signal path and a sample signal path in order to evaluate the intensity of reference signal 712, sample signal 714, and an electronic offset voltage $V_{offset}$. In the embodiment illustrated in FIG. 13A, the input value of reference signal 712 (as measured, for example, by reference photodetector 632 in FIG. 9A) and the input value of sample signal 714 (as measured, for example, by sample photodetector 634 in FIG. 9A) are illustrated. The combined input values of reference signal 712 and sample signal 714 are also illustrated in FIG. 13A as combined signal 716.

Figure 14A:
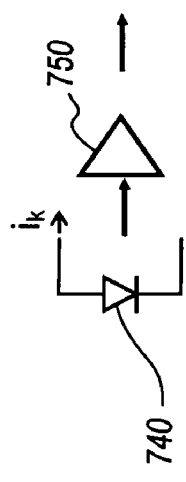
FIG. 14A is an illustration of an exemplary signal conditioner connected to the output of a photodetector.
Figure 14B:
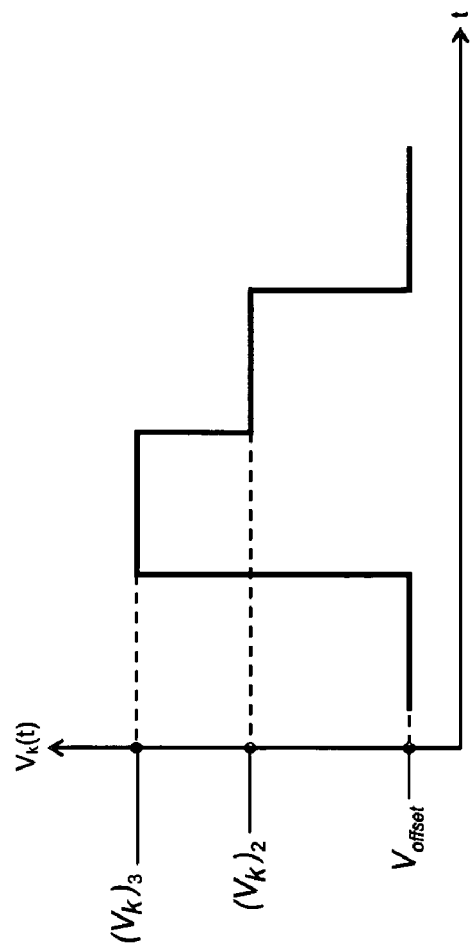
FIG. 14B is an exemplary representation of the voltage levels of a signal generated at the output of the signal conditioner in FIG. 14A.

FIG. 14B is an exemplary representation of a signal generated at the output of a signal conditioner 750 attached to the output of a photodetector 740 in a fluid analysis module employing modulator 720 (FIG. 13B). In at least one embodiment, the signal output at signal conditioner 750 comprises a $V_{offset}$ portion representing an offset voltage generated by the electronics associated with a fluid analysis module, a second signal $(V_k)_2$ representing the portion of voltage contributed to the output signal by reference signal 712 (FIG. 13A), plus $V_{offset}$, and a third signal $(V_k)_3$ representing the portion of voltage contributed to the output signal by sample signal 714 (FIG. 13A), plus $V_{offset}$. Generally speaking, $V_{offset}$ may either be measured when a fluid analysis module is shut off, or computed based on various known values (such as first and second signals $(V_k)_2$, $(V_k)_3$).

As with signals 633 and 642 in FIG. 12, signals $(V_k)_2$, $(V_k)_3$, and $V_{offset}$ may be digitized by an A/D converter (such as A/D converter 670 in FIG. 9A) and measured. Advantageously, because $(V_k)_2$ and $(V_k)_3$ represent the contributions of reference signal 712 (FIG. 13A) and sample signal 714 (FIG. 13A) to the signal output at signal processor 750, the optical density of a sample may then also be estimated using the following equation:

$$OD_k = \log\left(\frac{(V_k)_3 - (V_k)_{offset}}{(V_k)_2 - (V_k)_{offset}}\right) \qquad (18)$$

As described previously, in one preferred embodiment of the present invention the signal separation assembly 130 (FIGS. 1A-1B) may comprise a tunable spectrometer. In the case of a tunable spectrometer, as compared with a fixed wavelength spectrometer previously described, the shape and position of the channel transfer function may be controlled by an external command signal X, as illustrated in FIG. 15A. In practice, a tunable spectrometer leads to a channel transfer function $f_k(\lambda, X)$. Therefore, by changing X with time (X(t)), it is possible to perform spectral scanning. The function X(t) describes the correspondence between time and wavelength scanning. Seen from the frequency domain, as the wavelength range is scanned with time, it introduces an additional time dependent modulation of either signal phase or amplitude. The amplitude or phase modulation generated by the scanning may be demodulated by either amplitude or phase demodulation techniques. The resulting amplitude or phase in function of time may be reprocessed using the same equations as described for the fixed wavelength spectrometer above. The processing results in an estimation of OD as a function of time. Details of signal processing are not provided herein as such features are known to persons skilled in the art. As X(t) is known, OD(t) can then be translated in the wavelength domain. Seen for the time domain, one preferred approach to determine optical density is to use a stepping function for X(t). FIG. 15B illustrates such a function wherein X(t) is defined by the interval during which it is kept constant. Therefore, the scanning is done step by step. In this, for each step, the tunable spectrometer may be kept in one given spectral state, i.e., for each step processing techniques described for a fixed wavelength static case may be reapplied, as depicted in FIG. 15C. Furthermore, the modulator 120 (FIGS. 1A-1B) may be synchronized with the scanning signal. For example, in some embodiments described herein, signal acquisition may need to be synchronized with chopper wheel rotation. In this, synchronization of the modulator with the scanning signal makes it possible to minimize dead measurement time.

Accordingly, by shifting the frequency, phase, or other temporal aspect of a continuously transmitted reference and sample signal using one or more of the above-described exemplary modulators, the fluid analysis module of the present invention enables the separation and distinction of these input signals at the module's output. Based on the values of these separated signals, the electronics assembly of a fluid analysis module may then estimate the optical density of a fluid sample. As is known to those of skill in the art, this computed optical density enables a user to determine the presence and/or amount of various chemical compositions in a fluid sample, thereby enabling the user to effectively analyze the formation fluid. More specifically, by (1) continuously transmitting a reference signal and a sample signal, (2) modulating these signals, (3) separating these signals using an electronics assembly, and (4) computing the optical density of the fluid sample, the fluid analysis module of the present invention effectively compensates, in real-time, for drift in the light sources, photodetectors, and processing electronics used in analyzing formation fluids. Changes in temperature in a borehole and/or the tools lowered into such a borehole are thus accounted for in real-time, thereby increasing the overall accuracy and reliability of the fluid analysis module.

For the purposes of this disclosure, all estimated optical densities discussed herein have assumed that the light transmitted by a light source is equally split among a sample signal and a reference signal. In reality, however, light transmitted by a light source is not typically equally split between the reference and sample signals. To correct for any errors in this estimated amount, a correction coefficient must be applied to the estimated optical density. Any such correction coefficient must account for, for example, the actual ratio by which light transmitted by a light source is split among the reference signal and sample signal. In at least one embodiment, this ratio may be simply evaluated by splitting light from a light source in a non-absorbing sample, such as air. The measured ratio of light may then be used to correct the estimated optical density.

The preceding description has been presented only to illustrate and describe the invention and some examples of its implementation. This exemplary description is not intended to be exhaustive or to limit the invention to any precise form disclosed. Many modifications and variations are possible in light of the above teaching. For example, one of ordinary skill in the art will appreciate that the principles, methods and apparatuses disclosed herein are applicable to many oilfield operations, including MWD, LWD, PL and wireline operations.

As used throughout the specification and claims, the terms "borehole" or "downhole" refer to a subterranean environment, particularly in a borehole. The words "including" and "having," as used in the specification and claims, have the same meaning as the word "comprising." The preceding description is also intended to enable others skilled in the art to best utilize the invention in various embodiments and aspects and with various modifications as are suited to the particular use contemplated. It is intended that the scope of the invention be defined by the following claims.

What is claimed is:

1. A downhole apparatus for performing real-time analysis of a subterranean formation fluid, comprising:
    a light source configured to transmit at least a sample signal through a sample of the subterranean formation fluid and a reference signal;
    a modulator for modulating the sample and reference signals,
    a signal separation assembly for separating the modulated sample signal from the modulated reference signal, wherein the signal separation assembly comprises a spectrometer,
    at least one photodetector configured to continuously detect the sample and reference signals;
    an electronics assembly configured to compensate for drift in the detected sample signal in real-time based on the value of the detected reference signal.

2. The apparatus according to claim 1, wherein the spectrometer is a fixed wavelength spectrometer or a tunable spectrometer.

3. The apparatus according to claim 1, wherein the modulator modulates the sample signal and the reference signal at different frequencies.

4. The apparatus according to claim 1, wherein the modulator generates a phase shift between the sample signal and the reference signal.

5. The apparatus according to claim 3, wherein the modulator comprises:
    a first optical chopper configured to modulate the sample signal at a first frequency;
    a second optical chopper configured to modulate the reference signal at a second frequency differing from the first frequency.

6. The apparatus according to claim 3, wherein the modulator comprises a single optical chopper, the single optical chopper comprising:
    a first circular row of apertures configured to modulate the sample signal;
    a second circular row of apertures configured to modulate the reference signal;
    wherein the number of apertures in the first circular row differs from the number of apertures in the second circular row.

7. The apparatus according to claim 4, wherein the modulator comprises a single optical chopper;
    the sample signal is positioned to contact the single optical chopper at a first position;
    the reference signal is positioned to contact the single optical chopper at a second position;
    the second position is separated from the first position by a desired phase shift angle.

8. The apparatus according to claim 7, further comprising:
    a sample photodetector positioned to detect the phase of the sample signal;
    a reference photodetector positioned to detect the phase of the reference signal.

9. A downhole apparatus for performing real-time analysis of a subterranean formation fluid, comprising:
    a light source configured to transmit at least a sample signal through a sample of the subterranean formation fluid and a reference signal;
    a modulator for modulating the sample and reference signals,
        wherein the modulator generates a phase shift between the sample signal and the reference signal;
        wherein the modulator comprises a single optical chopper;
        wherein the single optical chopper comprises a single aperture for modulating the sample and reference signals;
    the sample signal is positioned to contact the single optical chopper at a first position;

the reference signal is positioned to contact the single optical chopper at a second position;

the second position is separated from the first position by a desired phase shift angle;

at least one photodetector configured to continuously detect the sample and reference signals;

an electronics assembly configured to compensate for drift in the detected sample signal in real-time based on the value of the detected reference signal.

10. The apparatus according to claim 9, wherein the electronics assembly is configured to compensate for drift in the detected sample signal based on the value of the detected reference signal and an offset voltage generated by the electronics assembly.

11. The apparatus according to claim 1, wherein the light source is a wavelength tunable light source or a broad-spectrum light source.

12. The apparatus according to claim 11, wherein the light source is an incandescent lamp, a light-emitting diode (LED), a monochromator, or a tunable laser diode.

13. A downhole apparatus for performing real-time analysis of a subterranean formation fluid, comprising:

a light source configured to transmit at least a sample signal through a sample of the subterranean formation fluid and a reference signal;

a modulator for modulating the sample and reference signals, wherein the modulator comprises a digital modulator;

at least one photodetector configured to continuously detect the sample and reference signals;

an electronics assembly configured to compensate for drift in the detected sample signal in real-time based on the value of the detected reference signal.

14. A method for analyzing a subterranean formation fluid downhole, comprising:

extracting the subterranean formation fluid in downhole;

transmitting a sample signal through a sample of the extracted subterranean formation fluid;

continuously transmitting a reference signal;

modulating the sample and reference signals;

separating the modulated sample signal from the modulated reference signal by using a signal separation assembly with a spectrometer;

continuously detecting the sample and reference signals using at least one photodetector;

correcting drift in the detected sample signal in real-time based on the value of the detected reference signal.

15. The method according to claim 14, further comprising:

inserting a downhole sampling tool into a borehole;

drawing down the sample of the subterranean formation fluid.

16. The method according to claim 14, wherein modulating the sample and reference signals comprises modulating the sample signal and the reference signal at different frequencies.

17. The method according to claim 14, wherein modulating the sample and reference signals comprises generating a phase shift between the sample signal and the reference signal.

18. The method according to claim 16, wherein modulating the sample and reference signals comprises:

modulating the sample signal at a first frequency using a first optical chopper;

modulating the reference signal at a second frequency differing from the first frequency using a second optical chopper.

19. The method according to claim 16, wherein modulating the sample and reference signals comprises:

providing a first circular row of apertures in the modulator to modulate the sample signal;

providing a second circular row of apertures in the modulator to modulate the reference signal;

wherein the number of apertures in the first circular row differs from the number of apertures in the second circular row.

20. The method according to claim 17, further comprising:

positioning the sample signal to contact the modulator at a first position;

positioning the reference signal to contact the modulator at a second position;

wherein the second position is separated from the first position by a desired phase shift angle.

21. The method according to claim 20, further comprising:

positioning a sample photodetector to detect the phase of the sample signal;

positioning a reference photodetector to detect the phase of the reference signal.

22. The method according to claim 21, further comprising:

correcting drift in the detected sample signal by compensating for drift in the detected sample signal based on the value of the detected reference signal and an offset voltage generated by the electronics assembly.

23. The method according to claim 14, wherein modulating the sample and reference signals comprises digitally modulating the sample and reference signals.

24. A method for analyzing a downhole fluid, comprising:

transmitting a sample signal through a sample of the downhole fluid using a light source;

transmitting a reference signal using the light source;

modulating the sample and reference signals;

separating the modulated sample signal from the modulated reference signal by using a signal separation assembly with a spectrometer;

continuously measuring the sample signal and reference signal to compensate for drift in the sample signal in real-time, wherein the analyzing is performed downhole.

25. The method of claim 24, further comprising communicating the measurements uphole to surface electronics.

26. A downhole apparatus for performing real-time analysis of a subterranean formation fluid, comprising:

a downhole sampling assembly for sampling the subterranean formation fluid;

a light source;

a reference signal continuously transmitted by the light source;

a sample signal transmitted by the light source through a sample of the subterranean formation fluid extracted by the downhole sampling assembly;

a modulator for modulating the sample and reference signals at different frequencies;

a signal separation assembly for separating the modulated sample signal from the modulated reference signal, wherein the signal separation assembly comprises a spectrometer;

at least one photodetector configured to continuously detect the sample and reference signals;

an electronics assembly configured to demodulate the sample signal and the reference and to compensate for drift in the detected sample signal in real-time based on the value of the detected reference signal.

27. An apparatus for performing real-time analysis of a subterranean formation fluid, comprising:

a downhole tool, The downhole tool comprising a fluid analysis module, the fluid analysis module comprising:

a light source configured to transmit at least a sample signal through a sample of the subterranean formation fluid and a reference signal;

a modulator for modulating the sample and reference signals;

a signal separation assembly for separating the modulated sample signal from the modulated reference signal. wherein the signal separation assembly comprises a spectrometer;

at least one photodetector configured to continuously detect the sample and reference signals;

an electronics assembty configured to compensate for drift in the detected sample signal in real-time based on the value of the detected reference signal.

\* \* \* \* \*